US010570174B2

(12) United States Patent
Wormser

(10) Patent No.: US 10,570,174 B2
(45) Date of Patent: Feb. 25, 2020

(54) PEPTIDES FOR THE TREATMENT OF MALIGNANT PROLIFERATIVE DISEASES

(71) Applicant: Yissum Research Development Company of the Hebrew University of Jerusalem Ltd., Jerusalem (IL)

(72) Inventor: Uri Wormser, Jerusalem (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 15/549,068

(22) PCT Filed: Feb. 7, 2016

(86) PCT No.: PCT/IL2016/050137
§ 371 (c)(1),
(2) Date: Aug. 4, 2017

(87) PCT Pub. No.: WO2016/125172
PCT Pub. Date: Aug. 11, 2016

(65) Prior Publication Data
US 2018/0037607 A1 Feb. 8, 2018

Related U.S. Application Data

(60) Provisional application No. 62/113,452, filed on Feb. 8, 2015.

(51) Int. Cl.
*C07K 7/06* (2006.01)
*C07K 7/08* (2006.01)
*C07K 14/47* (2006.01)
*A61K 38/04* (2006.01)

(52) U.S. Cl.
CPC ............... *C07K 7/06* (2013.01); *A61K 38/04* (2013.01); *C07K 7/08* (2013.01); *C07K 14/47* (2013.01)

(58) Field of Classification Search
None
See application file for complete search history.

(56) References Cited

U.S. PATENT DOCUMENTS

| 6,468,537 | B1 | 10/2002 | Datta et al. |
| 7,238,656 | B2 | 7/2007 | Wormser |
| 7,528,227 | B2 | 5/2009 | Wormser |
| 2008/0167249 | A1* | 7/2008 | Wormser ............... A61K 35/36 514/1.7 |
| 2009/0215700 | A1* | 8/2009 | Asami ................. C07K 14/4703 514/1.3 |

FOREIGN PATENT DOCUMENTS

| WO | 95/33765 A1 | 12/1995 |
| WO | 2005/090387 A2 | 9/2005 |
| WO | 2011/086553 A1 | 7/2011 |
| WO | 2012/029061 A2 | 3/2012 |

OTHER PUBLICATIONS

Pisal et al., "Delivery of Therapeutic Proteins," J. Pharma. Sci. 99:2557-2575 (2010) (Year: 2010).*
Aggarwal et al., "Inflammation and cancer: How hot is the link?" Biochem. Pharamcol. 72:1605-1621 (2006) (Year: 2006).*
Amaria et al., (2008) Immunomodulatory therapy in multiple sclerosis and breast cancer risk: a case report and literature review. Clinical breast cancer, 8(5), 449-452.
Brodsky et al., (2008) From topical antidote against skin irritants to a novel counter-irritating and anti-inflammatory peptide. Toxicology and applied pharmacology, 229(3), 342-350.
Caspi, (2008) Immunotherapy of autoimmunity and cancer: the penalty for success. Nature reviews immunology, 8(12), 970-976.
Gérard et al., (2009) Immunotherapy in the landscape of new targeted treatments for non-small cell lung cancer. Molecular oncology, 3(5-6), 409-424.
Hong et al., (2005) Induction of CD4+ CD25+ regulatory T cells by copolymer-I through activation of transcription factor Foxp3. Proceedings of the National Academy of Sciences of the United States of America, 102(18), 6449-6454.
Isidro-Llobet et al., (2009) Amino acid-protecting groups. Chemical reviews, 109(6), 2455-2504.
Merrifield, (1963) Solid phase peptide synthesis. I. The synthesis of a tetrapeptide. Journal of the American Chemical Society, 85(14), 2149-2154.
Pasare et al., (2005) Toll-like receptors: linking innate and adaptive immunity. Mechanisms of Lymphocyte Activation and Immune Regulation X, 11-18.
Penton-Rol et al., (2008) Treatment with type I interferons induces a regulatory T cell subset in peripheral blood mononuclear cells from multiple sclerosis patients. International immunopharmacology, 8(6), 881-886.
Shapira et al., (2010) Amelioration of experimental autoimmune encephalitis by novel peptides: involvement of T regulatory cells. Journal of autoimmunity, 35(1), 98-106.
Wormser et al., (2012) Protective effect of a novel peptide against methylmercury-induced toxicity in rat primary astrocytes. Neurotoxicology, 33(4), 763-768.

* cited by examiner

*Primary Examiner* — Julie Ha
*Assistant Examiner* — Kristina M Hellman
(74) *Attorney, Agent, or Firm* — J.A. Lindeman & Co., PLLC; Jeffrey Lindeman; Sulay Jhaveri

(57) ABSTRACT

Synthetic peptides containing chemical modifications having anti-tumor properties are provided. Further provided are pharmaceutical compositions including the peptides and use thereof for treating proliferative and neoplastic diseases such as cancer.

20 Claims, 18 Drawing Sheets
Specification includes a Sequence Listing.

SEQUENCE LISTING

```
<160> NUMBER OF SEQ ID NOS: 27

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa= Arg(Pbf)
```

<400> SEQUENCE: 1

Lys Gly His Tyr Ala Glu Xaa Val Gly
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X=Arg(Pbf)

<400> SEQUENCE: 2

Lys Gly His Tyr Xaa Ala Glu Val Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X=Arg(Pbf)

<400> SEQUENCE: 3

Glu Ala Tyr His Gly Lys Xaa Gly Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: X=Arg(NO2)

<400> SEQUENCE: 4

Lys Gly His Tyr Ala Glu Xaa Val Gly
1               5

<210> SEQ ID NO 5
<211> LENGTH: 9
<212> TYPE: PRT
<213> ORGANISM: Homo sapiens

<400> SEQUENCE: 5

Lys Gly His Tyr Ala Glu Arg Val Gly
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is selected from Ala-Glu-Arg(Z), Ala-Arg(Z)-Glu and Arg(Z)-Ala-Glu, Z is Pbf or NO2

<400> SEQUENCE: 6

Lys Gly His Tyr Xaa Val Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys and alkyl-Lys
<220> FEATURE:
<221> NAME/KEY: MISC_FEATURE
<222> LOCATION: (7)..(7)
<223> OTHER INFORMATION: X=Arg(Pbf)
<220> FEATURE:
<221> NAME/KEY: MISC_FEATURE
<222> LOCATION: (9)..(9)
<223> OTHER INFORMATION: X is selected from Gly, Gly-amide, Gly-alcohol
      and Gly-ester

<400> SEQUENCE: 7

Xaa Gly His Tyr Ala Glu Xaa Val Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys and alkyl-Lys
<220> FEATURE:
<221> NAME/KEY: MISC_FEATURE
<222> LOCATION: (5)..(5)
<223> OTHER INFORMATION: X=Arg(Pbf)
<220> FEATURE:
<221> NAME/KEY: MISC_FEATURE
<222> LOCATION: (9)..(9)
<223> OTHER INFORMATION: X is selected from Gly, Gly-amide, Gly-alcohol
      and Gly-ester

<400> SEQUENCE: 8

Xaa Gly His Tyr Xaa Ala Glu Val Xaa
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys and alkyl-Lys
<220> FEATURE:
<221> NAME/KEY: MISC_FEATURE
<222> LOCATION: (7)..(7)
<223> OTHER INFORMATION: X=Arg(NO2)
<220> FEATURE:
<221> NAME/KEY: MISC_FEATURE
<222> LOCATION: (9)..(9)
<223> OTHER INFORMATION: X is selected from Gly, Gly-amide, Gly-alcohol
      and Gly-ester

```
<400> SEQUENCE: 9

Xaa Gly His Tyr Ala Glu Xaa Val Xaa
 1               5

<210> SEQ ID NO 10
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (7)..(7)
<223> OTHER INFORMATION: X is Arg(Pbf) or Arg(NO2)
<220> FEATURE:
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 10

Xaa Gly His Tyr Ala Glu Xaa Val Xaa
 1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (6)..(6)
<223> OTHER INFORMATION: X is Arg(Pbf) or Arg(NO2)
<220> FEATURE:
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 11

Xaa Gly His Tyr Ala Xaa Glu Val Xaa
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (5)..(5)
<223> OTHER INFORMATION: X is Arg(Pbf) or Arg(NO2)
<220> FEATURE:
```

```
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 12

Xaa Gly His Tyr Xaa Ala Glu Val Xaa
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (4)..(4)
<223> OTHER INFORMATION: X is Arg(Pbf) or Arg(NO2)
<220> FEATURE:
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 13

Xaa Gly His Xaa Tyr Ala Glu Val Xaa
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (3)..(3)
<223> OTHER INFORMATION: X is Arg(Pbf) or Arg(NO2)
<220> FEATURE:
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 14

Xaa Gly Xaa His Tyr Ala Glu Val Xaa
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
```

```
<220> FEATURE:
<221> NAME/KEY: MISC_FEATURE
<222> LOCATION: (2)..(2)
<223> OTHER INFORMATION: X is Arg(Pbf) or Arg(NO2)
<220

-continued

```
<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is Arg(Pbf) or Arg(NO2)

<400> SEQUENCE: 19

Lys Gly His Tyr Xaa Ala Glu Val Gly
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is Arg(Pbf) or Arg(NO2)

<400> SEQUENCE: 20

Lys Gly His Xaa Tyr Ala Glu Val Gly
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is Arg(Pbf) or Arg(NO2)

<400> SEQUENCE: 21

Lys Gly Xaa His Tyr Ala Glu Val Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is Arg(Pbf) or Arg(NO2)

<400> SEQUENCE: 22

Lys Xaa Gly His Tyr Ala Glu Val Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: X is Arg(Pbf) or Arg(NO2)
```

```
<400> SEQUENCE: 23

Lys Gly His Tyr Ala Glu Val Xaa Gly
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is Arg(Pbf) or Arg(NO2)

<400> SEQUENCE: 24

Xaa Lys Gly His Tyr Ala Glu Val Gly
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: X is Arg(Pbf) or Arg(NO2)

<400> SEQUENCE: 25

Lys Gly His Tyr Ala Glu Val Gly Xaa
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Arg(Z), acyl-Arg(Z),
      alkyl-Arg(Z) and Arg(Z) modified with a permeability enhancing or
      targeting moiety, Z is Pbf or NO2
<220> FEATURE:
<221> NAME/KEY: MISC_FEATURE
<222> LOCATION: (9)..(9)
<223> OTHER INFORMATION: X is selected from Gly, Gly-amide, Gly-alcohol,
      Gly-ester and Gly modified with a permeability-enhancing or
      targeting moiety

<400> SEQUENCE: 26

Xaa Lys Gly His Tyr Ala Glu Val Xaa
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is selected from Lys, acyl-Lys, alkyl-Lys and
      Lys modified with a permeability-enhancing or targeting moiety
<220> FEATURE:
<221> NAME/KEY: MISC_FEATURE
<222> LOCATION: (9)..(9)
```

```
<223> OTHER INFORMATION: X is selected from Arg(Z), Arg(Z)-amide,
      Arg(Z)-alcohol, Arg(Z)-ester and Arg(Z) modified with a
      permeability-enhancing or targeting moiety, Z is Pbf or NO2

<400> SEQUENCE: 27

Lys Gly His Tyr Ala Glu Val Gly Xaa
 1               5
```

PEPTIDES FOR THE TREATMENT OF MALIGNANT PROLIFERATIVE DISEASES

SEQUENCE LISTING

The Sequence Listing submitted in text format (.txt) filed on Aug. 4, 2017, named "SequenceListing.txt", created on Jul. 27, 2017, 11.1 KB), is incorporated herein by reference.

FIELD OF THE INVENTION

The present invention relates to chemically modified peptides having anti-tumor properties, pharmaceutical compositions comprising the peptides, and use thereof for treating proliferative and neoplastic diseases such as cancer.

BACKGROUND OF THE INVENTION

Cancer is the leading cause of death in most developed countries, and as the average age of the population continues to rise, so do the numbers of diagnosed cases of cancer. Cancer is characterized by uncontrolled growth and spread of abnormal cells. Despite advances in cancer diagnosis and treatment over the years, existing therapies still have limitations. Surgery and radiotherapy, for example, may be curative only if the cancer is diagnosed early enough, while current drug therapies, e.g., for metastatic diseases, seldom offer a long-term cure. Over the last decade, new strategies to treat cancer patients have emerged. Unlike traditional cytotoxic therapies, the new strategies focus more on the tumor itself and its supportive microenvironment. Additional approaches for cancer treatment include preventing angiogenesis and activating the immune system, for example using cancer vaccines and cell therapies. The main aim is to improve anti-tumor efficacy while reducing toxic and other adverse effects in the patients. However, even with new therapies entering the market, there is an unmet medical need for new drugs effective as monotherapy or in combination with existing agents as a first line therapy in various types of cancer, and as second and third line therapies in treatment of resistant tumors.

For example, lung cancer is one of the most fatal cancers worldwide, causing more than 1.2 million deaths each year, according to recent reports. Non-small cell lung cancer (NSCLC) cases are the vast majority of all cases of lung cancer. NSCLC is particularly fatal since most of the patients are diagnosed when the disease has already progressed to a relatively advanced stage, usually at incurable stages IIIB or IV. According to an analysis done by the International Association for the Study of Lung Cancer (IASLC), the 5-year survival rate is 73% at stage IA, 58% at stage IB, 46% at stage IIA, 36% at stage IIB and only 24% if patient was diagnosed at stage IIIA of NSCLC disease. Besides the need for earlier diagnosis, there is a great need for additional, more effective, therapies. In resected NSCLC, the only approved adjuvant therapy is chemotherapy using drugs such as paclitaxel, cisplatin, and vinblastine, which provide a limited clinical benefit. In completely resected NSCLC, for example, an absolute benefit of elevating 5-year survival rate by only 5.4% (on average) was demonstrated in a pooled analysis of five large trials of adjuvant cisplatin-based chemotherapy carried out by the LACE collaborative group. Moreover, 34% of the patients in these trials did not complete the planned number of cycles due to toxicity, treatment-emergent adverse events, and adverse effects. The benefit of chemotherapy treatment is still under debate for stage I.

As another example, melanoma, a disease which occurs when melanocytes undergo mutational changes and become malignant, causes about 50,000 deaths annually worldwide, and its incidence continues to increase. The incidence of malignant melanoma has increased fivefold from 1980 to 2009. If the tumor is detected early, before invading the dermis, surgical excision is curative in approximately 99% of patients. Unfortunately, melanoma is not always diagnosed at early stage, resulting in poor prognosis. Currently, the main treatments for melanoma are surgery, radiotherapy and chemotherapy. Surgery can provide efficient tumor resection and cure the patient if there are no metastases. Radiation therapy is used in severe cases, and in conjunction with surgery, to increase the efficiency of treatment. Enormous advances in the treatment of melanoma have occurred in recent years as a result of improved understanding of the molecular pathways driving this malignancy as well as the critical importance of the role of the immune system in this process. However, there still remains a need for more effective and safer melanoma therapies.

U.S. Pat. No. 6,468,537 discloses peptides derived from nucleosomal histone proteins which are useful for delaying the onset and progression of systemic lupus erythematosus. Among other peptides, a peptide of the sequence Leu-Arg-Lys-Gly-Asn-Tyr-Ala-Glu-Arg-Val-Gly-Ala-Gly-Ala-Pro (SEQ ID NO: 9 of U.S. Pat. No. 6,468,537) is disclosed.

U.S. Pat. Nos. 7,238,656 and 7,528,227 disclose, inter alia, histone H2A-derived peptides and derivatives thereof, and use of these peptides and derivatives for treating inflammatory diseases. Among other peptides, a peptide of the sequence H-Lys-Gly-His-Tyr-Ala-Glu-Arg-Val-Gly-OH is disclosed (SEQ ID NO: 13 of U.S. Pat. No. 7,238,656, SEQ ID NO: 1 of U.S. Pat. No. 7,528,227).

There remains an unmet need for safe and efficient agents that are useful in treating malignant proliferative diseases, having reduced or no side effects.

SUMMARY OF THE INVENTION

The present invention according to some aspects provides synthetic chemically-modified peptides having anti-tumor properties. The present invention further provides pharmaceutical compositions comprising the modified peptides and methods of use thereof in treating malignant proliferative diseases. In particular, the modified peptides disclosed herein are useful for attenuating or inhibiting tumor growth and tumor metastasis, and eradicating solid tumors, non-solid malignancies and precancerous conditions.

The modified peptides disclosed herein comprise according to some embodiments a core sequence of 9 amino acids in which a side chain of an arginine residue present in the sequence is modified with an attached chemical group, designated as Z, selected from Pbf (2,2,4,6,7-pentamethyl-dihydrobenzofuran-5-sulfonyl) and Nitro ($NO_2$), as follows: Lys-Gly-His-Tyr-$X_1$-$X_2$-$X_3$-Val-Gly (SEQ ID NO: 6), wherein $X_1$-$X_2$-$X_3$ represent Ala-Glu-Arg(Z), Ala-Arg(Z)-Glu or Arg(Z)-Ala-Glu. This core sequence is a non-naturally occurring modification of the sequence Lys-Gly-His-Tyr-Ala-Glu-Arg-Val-Gly (SEQ ID NO: 5), which corresponds to amino acids 37-45 of a histone H2A variant found in human and mouse, also known as H2AX (NCBI accession numbers NP_002096 and NP_034566, respectively).

The present invention is based in part on the unexpected discovery that synthetic modified peptides composed of the aforementioned core amino acid sequence are highly effective in attenuating and eradicating the growth of tumors. The modified peptides are particularly effective in inhibiting or treating solid tumors, including for example lung, mammary, and melanoma tumors, as exemplified hereinbelow in mice. Not only did the modified peptides attenuate tumor growth, the modified peptides were also shown to decrease occurrence and number of tumor metastatic foci.

The modified peptides were found to be effective in attenuating tumor growth and tumor metastasis when administered both parenterally and orally, as exemplified hereinbelow. Advantageously, the modified peptides were found to be very potent and their effect was observed at nanogram/kg doses in several different mouse models. On the other hand, administration of very high dosages of the modified peptides to tumor cell-injected mice did not cause any observed deleterious effects, thus these modified peptides are promising as an efficacious medication for treating a variety of different cancers without causing undesired serious side effects.

According to one aspect, the present invention provides a peptide of 9-15 amino acids comprising the sequence Lys-Gly-His-Tyr-$X_1$-$X_2$-$X_3$-Val-Gly (SEQ ID NO: 6), wherein $X_1$-$X_2$-$X_3$ represent a sequence selected from the group consisting of Ala-Glu-Arg(Z), Ala-Arg(Z)-Glu and Arg(Z)-Ala-Glu, wherein Z is selected from the group consisting of Pbf (2,2,4,6,7-pentamethyldihydrobenzofuran-5-sulfonyl) and Nitro ($NO_2$).

Pbf is an arginine side chain protecting group commonly used in peptide synthesis, and the abovementioned Arg(Pbf) is the compound represented by the following formula (except that within the peptide sequence the amino and carboxy groups are bound to their adjacent moieties):

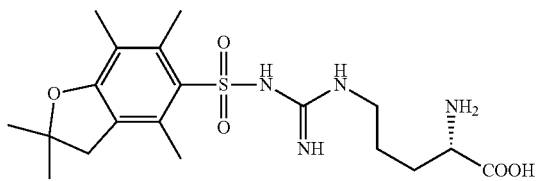 [SMILES: Cc1c(C)c(S(=O)(=O)NC(=N)NCCC[C@H](N)C(=O)O)c(C)c2c1OC(C)(C)C2]

Nitro is another arginine side chain protecting group commonly used in peptide synthesis, and the abovementioned Arg($NO_2$) is the compound represented by the following formula (except that within the peptide sequence the amino and carboxy groups are bound to their adjacent moieties):

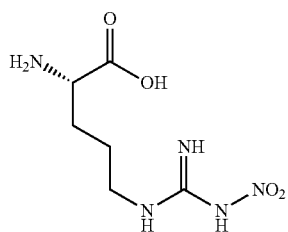 [SMILES: N=C(NCCC[C@H](N)C(=O)O)N[N+](=O)[O-]]

In some embodiments, the peptide comprises a sequence selected from the group consisting of:

```
                                        (SEQ ID NO: 1)
Lys-Gly-His-Tyr-Ala-Glu-Arg(Pbf)-Val-Gly;

(SEQ ID NO: 2)
Lys-Gly-His-Tyr-Arg(Pbf)-Ala-Glu-Val-Gly;
and (SEQ ID NO: 4)
Lys-Gly-His-Tyr-Ala-Glu-Arg(NO2)-Val-Gly.
```

In some embodiments, the peptide further comprises at least one modification selected from the group consisting of an amino-terminal modification and a carboxy-terminal modification. Each possibility represents a separate embodiment of the invention.

In some embodiments, the amino terminal modification is an amino blocking group selected from the group consisting of an acyl (e.g. acetyl) and alkyl (e.g., methyl). Each possibility represents a separate embodiment of the invention.

In some embodiments, the carboxy-terminal modification is a carboxyl blocking group selected from the group consisting of an amide, alcohol and an ester. Each possibility represents a separate embodiment of the invention.

According to some embodiments, the peptide is of 9-12 amino acids. According to some particular embodiments, the peptide is of 9 amino acids. Each possibility represents a separate embodiment of the present invention.

In some embodiments, the peptide is selected from the group consisting of:

```
                                           (SEQ ID NO: 7)
R1-Lys-Gly-His-Tyr-Ala-Glu-Arg(Pbf)-Val-Gly-R2;

(SEQ ID NO: 8)
R1-Lys-Gly-His-Tyr-Arg(Pbf)-Ala-Glu-Val-Gly-R2;
and (SEQ ID NO: 9)
R1-Lys-Gly-His-Tyr-Ala-Glu-Arg(NO2)-Val-Gly-R2,
``` wherein $R_1$ designates a hydrogen of an unmodified amino terminal group or is an amino blocking group selected from the group consisting of acyl and alkyl; and $R_2$ designates OH of an unmodified carboxy terminal group or is a carboxyl blocking group selected from the group consisting of an amide, alcohol and ester. Each possibility represents a separate embodiment of the present invention.

In some particular embodiments, the peptide is selected from the group consisting of:

```
                                           (SEQ ID NO: 1)
H-Lys-Gly-His-Tyr-Ala-Glu-Arg(Pbf)-Val-Gly-OH;

(SEQ ID NO: 2)
H-Lys-Gly-His-Tyr-Arg(Pbf)-Ala-Glu-Val-Gly-OH;
and (SEQ ID NO: 4)
H-Lys-Gly-His-Tyr-Ala-Glu-Arg(NO2)-Val-Gly-OH.
```

Each possibility represents a separate embodiment of the present invention.

In some embodiments, the peptide is conjugated to a moiety selected from the group consisting of a permeability-enhancing moiety (e.g. a fatty acid), a synthetic polymer, a carrier or targeting peptide, a carrier or targeting protein, and a sugar moiety.

According to another aspect of the present invention, a peptide is provided, selected from the group consisting of:

R₁-Lys-Gly-His-Tyr-Ala-Glu-Arg(Z)-Val-Gly-R₂; (SEQ ID NO: 10)

R₁-Lys-Gly-His-Tyr-Ala-Arg(Z)-Glu-Val-Gly-R₂; (SEQ ID NO: 11)

R₁-Lys-Gly-His-Tyr-Arg(Z)-Ala-Glu-Val-Gly-R₂; (SEQ ID NO: 12)

R₁-Lys-Gly-His-Arg(Z)-Tyr-Ala-Glu-Val-Gly-R₂; (SEQ ID NO: 13)

R₁-Lys-Gly-Arg(Z)-His-Tyr-Ala-Glu-Val-Gly-R₂; (SEQ ID NO: 14)

R₁-Lys-Arg(Z)-Gly-His-Tyr-Ala-Glu-Val-Gly-R₂; and (SEQ ID NO: 15)

R₁-Lys-Gly-His-Tyr-Ala-Glu-Val-Arg(Z)-Gly-R₂; (SEQ ID NO: 16)

wherein:

$R_1$ designates a hydrogen of an unmodified amino terminal group or is selected from the group consisting of: (i) an amino blocking group selected from acyl and alkyl, and (ii) a permeability-enhancing or targeting moiety;

$R_2$ designates OH of an unmodified carboxy terminal group or is selected from the group consisting of: (i) a carboxyl blocking group selected from an amide, alcohol and ester, and (ii) a permeability-enhancing or targeting moiety; and Z is selected from the group consisting of Pbf (2,2,4,6,7-pentamethyldihydrobenzofuran-5-sulfonyl) and Nitro ($NO_2$).

In some embodiments, the peptide is conjugated to a moiety selected from the group consisting of a fatty acid, a synthetic polymer, a carrier or targeting peptide, a carrier or targeting protein, and a sugar moiety.

According to another aspect, the present invention provides a pharmaceutical composition comprising the peptide according to the principles of the present invention as defined above or a conjugate comprising said peptide, and a pharmaceutically acceptable carrier, excipient or diluent.

According to an additional aspect, the present invention provides a pharmaceutical composition comprising the peptide of the present invention or a conjugate comprising said peptide, for use in treating cancer.

According to yet another aspect, the present invention provides a method of treating cancer comprising administering to a subject in need of such treatment a pharmaceutical composition comprising a therapeutically effective amount of the peptide of the present invention or a conjugate comprising said peptide.

According to some embodiments, the cancer is a solid tumor. According to additional embodiments, the cancer is a non-solid malignant disease.

According to some embodiments, the solid tumor is selected from the group consisting of lung cancer, colon cancer, breast cancer, pancreatic cancer, prostate cancer, melanoma, and ovarian cancer. According to certain embodiments, the cancer is lung cancer, breast cancer or melanoma. Each possibility represents a separate embodiment of the invention.

According to certain embodiments, the subject to be treated using the methods of the present invention is a human subject. According to other embodiments, the subject is a non-human mammal.

The methods of the present invention may be applicable to treat a subject during the active phase of the cancer, as well as following treatment to prevent relapse or reoccurrence of the cancer, or for treating minimal residual disease (MRD).

Other objects, features and advantages of the present invention will become clear from the following description, examples and drawings.

BRIEF DESCRIPTION OF THE FIGURES

In FIG. 1A, several dosages of YHI1 were orally administered at the indicated doses 8, 6, 4, and 1 day prior to tumor cell injection and thereafter up to 35 days, 3 times a week. Control mice received vehicle only (saline, oral). $p<0.05$ for 5 mg/kg group versus control, for the period of 23-35 days (Mann-Whitney test).

In FIG. 1B, several dosages of YHI1 were intraperitoneally (i.p.) administered 8, 6, 4 and 1 day prior to cell injection and thereafter up to 34 days, 3 times a week. Control mice received vehicle only (saline, i.p). $p<0.001$ and $p<0.01$ for 0.1 μg/kg group versus control and 1 μg/kg group versus control, respectively, for the period of 19-33 days; $p<0.001$ and $p<0.05$ for 0.1 μg/kg and 1 μg/kg groups, respectively, for the period of 16-33 days.

FIG. 8A shows histological sections (H&E, ×2) of lungs. Control (right), YHI1-treated (left). T=Tumor. FIG. 8B shows histological scores of control vs. YHI1-treated lungs. *p<0.02.

FIG. 12A shows histological sections (H&E, ×2) of lungs. Control (right), YHI1-treated (left). T=Tumor. FIG. 12B shows average histological scores of control vs. YHI1-treated lungs, ****p<0.0001.

DETAILED DESCRIPTION OF THE INVENTION

Figure 1A:
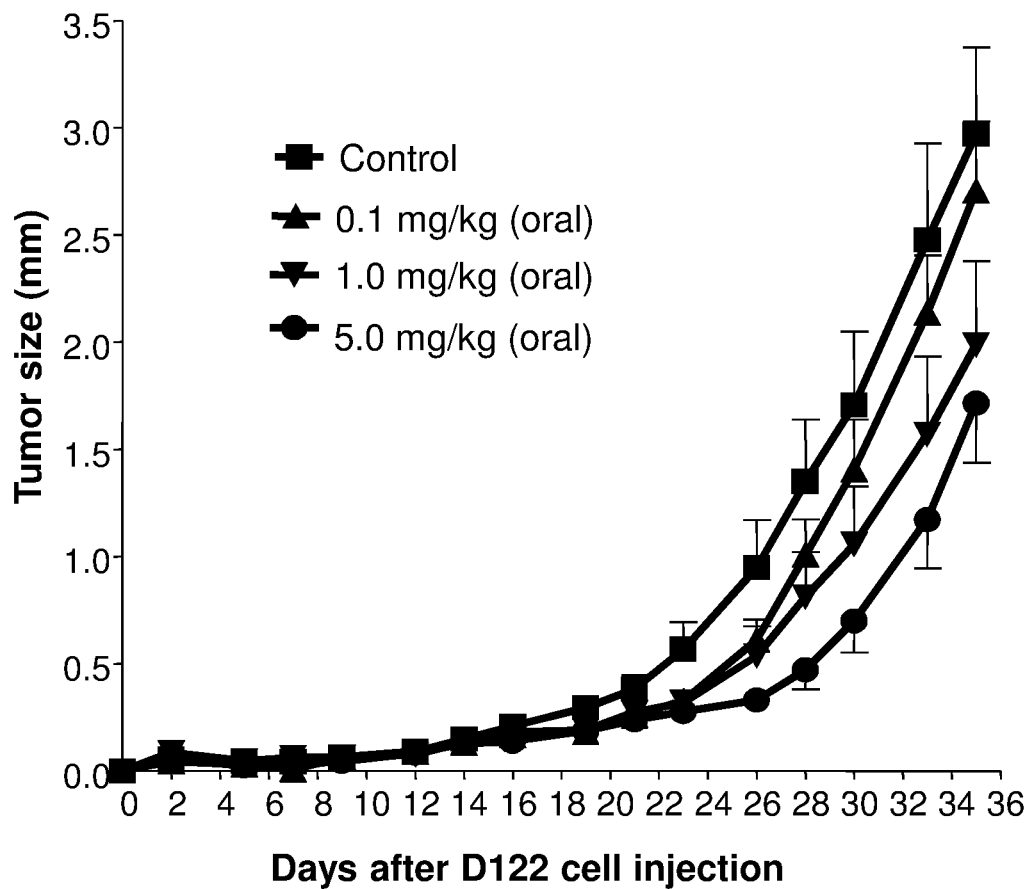
FIGS. 1A-1B show the effect of YHI1 on tumor growth in a mouse footpad model. Female C57BL/6 mice were injected in the footpads with D122 lung tumor cells (3LL Lewis lung carcinoma).

The present invention is directed, inter alia, to highly potent chemically modified peptides and use thereof for treating proliferative diseases. The modified peptides are useful for the treatment of malignant proliferative diseases. In some embodiments, the peptides are used for the treatment of benign proliferative diseases and benign tumors.

The present invention is based in part on the surprising finding that synthesis of the known anti-inflammatory peptide designated IIIM1 of the amino acid sequence KGHYAERVG (SEQ ID NO: 5; see, for example, U.S. Pat. No. 7,528,227), resulted in one specific batch which was devoid of anti-inflammatory activity. Examination of that batch revealed that it contained IIIM1, constituting about 94.5% of the peptide content, and an additional peptide, designated herein YHI1, with the same sequence of IIIM1 except that the side chain of the arginine at position 7 was protected with a Pbf protecting group: KGHYAER(Pbf)VG (SEQ ID NO: 1). YHI1 constituted about 5.5% of the peptide content in the batch. Further examination of YHI1 revealed that it is a highly potent anti-cancer agent, capable of exhibiting its anti-cancer activity at doses as low as tens of nanograms per 1 kg body weight when injected i.p 3 to 6 times per week. The effect was demonstrated in several mouse models of cancer. Advantageously, YHI1 exhibited its effect both on local tumor growth (when malignant cells were injected to mice subcutaneously), and on metastasis formation (when malignant cells were injected to mice intravenously). In some experiments, administration of lower doses of YHI1, e.g., 30 ng/kg or 10 ng/kg body weight of mouse, were as effective or more effective than a higher dose of 100 ng/kg body weight in inhibiting tumor growth and metastasis when injected ip 3 to 6 times per week.

In addition, variations (derivatives) of YHI1, one with the amino acid sequence KGHYR(Pbf)AEVG (SEQ ID NO: 2), designated herein YHI2, and another with the amino acid sequence KGHYAER($NO_2$)VG (SEQ ID NO: 4), designated herein YHI4, were also found to have anti-tumor activity.

Peptides

According to some embodiments, a synthetic peptide of 9-30 amino acids is provided, comprising the sequence Lys-Gly-His-Tyr-$X_1$-$X_2$-$X_3$-Val-Gly (SEQ ID NO: 6), wherein $X_1$-$X_2$-$X_3$ is selected from the group consisting of Ala-Glu-Arg(Z), Ala-Arg(Z)-Glu and Arg(Z)-Ala-Glu, wherein Z is an arginine side-chain protecting group selected from Pbf (2,2,4,6,7-pentamethyldihydrobenzofuran-5-sulfonyl) and Nitro ($NO_2$). In some embodiments, $X_1$-$X_2$-$X_3$ is selected from the group consisting of Ala-Glu-Arg(Z) and Arg(Z)-Ala-Glu. Each possibility represents a separate embodiment of the present invention.

In such peptide, the side-chain protected Arg residue is located at position 7 of SEQ ID NO: 6, at position 6 of SEQ ID NO: 6 or at position 5 of SEQ ID NO: 6. In some embodiments of the current invention, the side-chain protected Arg residue may be located at additional positions within the sequence. Thus, according to additional embodiments, a peptide of 9-30 amino acids is provided, comprising a sequence selected from the group consisting of:

```
                                            (SEQ ID NO: 17)
Lys-Gly-His-Tyr-Ala-Glu-Arg(Z)-Val-Gly;

(SEQ ID NO: 18)
Lys-Gly-His-Tyr-Ala-Arg(Z)-Glu-Val-Gly;

(SEQ ID NO: 19)
Lys-Gly-His-Tyr-Arg(Z)-Ala-Glu-Val-Gly;

(SEQ ID NO: 20)
Lys-Gly-His-Arg(Z)-Tyr-Ala-Glu-Val-Gly;

(SEQ ID NO: 21)
Lys-Gly-Arg(Z)-His-Tyr-Ala-Glu-Val-Gly;

(SEQ ID NO: 22)
Lys-Arg(Z)-Gly-His-Tyr-Ala-Glu-Val-Gly;
and (SEQ ID NO: 23)
Lys-Gly-His-Tyr-Ala-Glu-Val-Arg(Z)-Gly,
``` wherein Z is selected from the group consisting of Pbf (pentamethyl-2,3-dihydrobenzofuran-5-sulfonyl) and Nitro ($NO_2$). Each possibility represents a separate embodiment of the present invention.

In additional embodiments, the peptide comprises a sequence selected from: Arg(Z)-Lys-Gly-His-Tyr-Ala-Glu-Val-Gly (SEQ ID NO: 24) and Lys-Gly-His-Tyr-Ala-Glu-Val-Gly-Arg(Z) (SEQ ID NO: 25), wherein Z is selected from the group consisting of Pbf and $NO_2$. Each possibility represents a separate embodiment of the present invention.

Z according to some embodiments may be selected from additional arginine side-chain protecting groups. Additional side-chain protecting groups may be used provided that the anti-tumor activity of the peptide is maintained.

The term "side-chain protecting group" is an art-recognized term which refers to a chemical moiety coupled to a functional group of an amino acid side chain (R group in the general amino acid formula $H_2N-C(R)(H)-COOH$), to protect the functional group from forming undesired bonds and nonspecific reactions during solid-phase or solution peptide synthesis. Amino acid side-chain protecting groups, including arginine side-chain protecting groups, are reviewed, for example, in Isidro-Llobet et al., 2009, *Chem. Rev.*, 109: 2455-2504.

In some embodiments, Z is selected from the group consisting of Pbf (2,2,4,6,7-pentamethyldihydrobenzofuran-5-sulfonyl), Pmc (2,2,5,7,8-pentamethylchroman-6-sulfonyl), Mts (mesityl-2-sulfonyl), Mtr (4-methoxy-2,3,6-trimethylphenylsulfonyl), and MIS (1,2-dimethylindole-3-sulfonyl). Each possibility represents a separate embodiment of the present invention. In some particular embodiments, Z is Pbf.

In other embodiments, Z is Nitro ($NO_2$).

Additional arginine side chain protecting groups include ω-5-Dibenzosuberenyl (Suben), 5-Dibenzosuberyl (Sub), 2-Methoxy-5-dibenzosuberyl (MeSub), Trifluoroacetyl (tfa), ω,ω'-bis-Benzyloxycarbonyl (bis-Z) and ω,ω'-bis-Allyloxycarbonyl (Alloc). In some embodiments, Z is an arginine side-chain protecting group other than tosyl.

In some embodiments, a synthetic peptide of up to 30 amino acids is provided, comprising the amino acid sequence Lys-Gly-His-Tyr-Ala-Glu-Arg(Pbf)-Val-Gly (SEQ ID NO: 1), wherein Pbf is 2,2,4,6,7-pentamethyldihydrobenzofuran-5-sulfonyl. In some particular embodiments, the peptide consists of SEQ ID NO: 1 and is optionally modified with N-terminal and/or C-terminal blocking groups, as follows: $R_1$-Lys-Gly-His-Tyr-Ala-Glu-Arg(Pbf)-Val-Gly-$R_2$ (SEQ ID NO: 7), wherein $R_1$ designates an unmodified amino terminal group or is an amino blocking group selected from the group consisting of acyl and alkyl; and $R_2$ designates OH of an unmodified carboxy terminal group or is a carboxyl blocking group selected from the group consisting of an amide, alcohol and ester. In some embodiments, the peptide consists of SEQ ID NO: 1 and is optionally conjugated to a permeability-enhancing moiety (e.g. a fatty acid), a synthetic polymer, a carrier or targeting peptide, a carrier or targeting protein, and a sugar moiety. In some particular embodiments, the peptide is H-Lys-Gly-His-Tyr-Ala-Glu-Arg(Pbf)-Val-Gly-OH (SEQ ID NO: 1).

In some embodiments, a synthetic peptide of up to 30 amino acids is provided, comprising the amino acid sequence Lys-Gly-His-Tyr-Arg(Pbf)-Ala-Glu-Val-Gly (SEQ ID NO: 2), wherein Pbf is 2,2,4,6,7-pentamethyldihydrobenzofuran-5-sulfonyl. In particular embodiments, the peptide consists of SEQ ID NO: 2 and is optionally modified with N-terminal and/or C-terminal blocking groups, as follows: $R_1$-Lys-Gly-His-Tyr-Arg(Pbf)-Ala-Glu-Val-Gly-$R_2$ (SEQ ID NO: 8), wherein $R_1$ and $R_2$ are as defined above. In some embodiments, the peptide consists of SEQ ID NO: 2 and is optionally conjugated to a permeability-enhancing moiety (e.g. a fatty acid), a synthetic polymer, a carrier or targeting peptide, a carrier or targeting protein, and a sugar moiety. In some particular embodiments, the peptide is H-Lys-Gly-His-Tyr-Arg(Pbf)-Ala-Glu-Val-Gly-OH (SEQ ID NO: 2).

In additional embodiments, a synthetic peptide of up to 30 amino acids is provided, comprising the amino acid sequence Lys-Gly-His-Tyr-Ala-Glu-Arg($NO_2$)-Val-Gly (SEQ ID NO: 4). In particular embodiments, the peptide consists of SEQ ID NO: 4 and is optionally modified with N-terminal and/or C-terminal blocking groups, as follows: $R_1$-Lys-Gly-His-Tyr-Ala-Glu-Arg($NO_2$)-Val-Gly-$R_2$ (SEQ ID NO: 9), wherein $R_1$ and $R_2$ are as defined above. In some embodiments, the peptide consists of SEQ ID NO: 4 and is optionally conjugated to a permeability-enhancing moiety (e.g. a fatty acid), a synthetic polymer, a carrier or targeting peptide, a carrier or targeting protein, and a sugar moiety. In some particular embodiments, the peptide is H-Lys-Gly-His-Tyr-Ala-Glu-Arg($NO_2$)-Val-Gly-OH (SEQ ID NO: 4).

In some embodiments, a peptide is provided, selected from the group consisting of:

```
                                            (SEQ ID NO: 10)
R₁-Lys-Gly-His-Tyr-Ala-Glu-Arg(Z)-Val-Gly-R₂;

(SEQ ID NO: 11)
R₁-Lys-Gly-His-Tyr-Ala-Arg(Z)-Glu-Val-Gly-R₂;

(SEQ ID NO: 12)
R₁-Lys-Gly-His-Tyr-Arg(Z)-Ala-Glu-Val-Gly-R₂;

(SEQ ID NO: 13)
R₁-Lys-Gly-His-Arg(Z)-Tyr-Ala-Glu-Val-Gly-R₂;

(SEQ ID NO: 14)
R₁-Lys-Gly-Arg(Z)-His-Tyr-Ala-Glu-Val-Gly-R₂;

(SEQ ID NO: 15)
R₁-Lys-Arg(Z)-Gly-His-Tyr-Ala-Glu-Val-Gly-R₂;
and (SEQ ID NO: 16)
R₁-Lys-Gly-His-Tyr-Ala-Glu-Val-Arg(Z)-Gly-R₂;
``` wherein:

R$_1$ designates a hydrogen of an unmodified amino terminal group or is selected from the group consisting of: (i) an amino blocking group selected from acyl and alkyl, and (ii) a permeability enhancing or targeting moiety;

R$_2$ designates OH of an unmodified carboxy terminal group or is selected from the group consisting of: (i) a carboxyl blocking group selected from an amide, alcohol and ester, and (ii) a permeability enhancing or targeting moiety; and Z is selected from the group consisting of Pbf (2,2,4,6, 7-pentamethyldihydrobenzofuran-5-sulfonyl) and Nitro (NO$_2$).

Each possibility represents a separate embodiment of the present invention.

In additional embodiments, the peptide is selected from the group consisting of: R$_1$-Arg(Z)-Lys-Gly-His-Tyr-Ala-Glu-Val-Gly-R$_2$ (SEQ ID NO: 26) and R$_1$-Lys-Gly-His-Tyr-Ala-Glu-Val-Gly-Arg(Z)-R$_2$ (SEQ ID NO: 27), wherein Z is selected from the group consisting of Pbf and NO$_2$. Each possibility represents a separate embodiment of the present invention.

In some embodiments, peptides comprising or consisting of fragments of the peptides of the present invention are provided. In some embodiments, a peptide of 4-15 amino acids is provided, comprising at least 4 contiguous amino acids of any one of SEQ ID NOs: 1, 2, 4, 6-27 including Arg(Z), wherein Z is an arginine-side chain protecting group as defined above.

In some embodiments, the peptide comprising a peptide fragment is of 5-15 amino acids, for example 5, 6, 7, 8, 9, 10, 11, 12, 13, 14 or 15 amino acids. Each possibility represents a separate embodiment of the present invention.

A fragment of a peptide of the present invention may be used provided that the anti-tumor activity of the peptide is maintained.

The term "peptide" as used herein refers to a polymer of amino acid residues linked by peptide bonds. By "peptide" it is meant an amino acid sequence consisting of up to 50 amino acids, for example up to 40 amino acids, up to 30 amino acids, up to 20 amino acids or less. By "polypeptide" or "protein" it is meant an amino acid sequence of more than 50 amino acid residues.

The term "amino acid" refers to any one of the proteinogenic amino acids, including the 20 genetically-encoded amino acids, and also non-natural and/or amino acids that have been chemically modified (synthetic), each amino acid being characterized by having an amino and a carboxy terminus. The amino acids used in this invention are those which are available commercially or are available by routine synthetic methods. The amino acids are represented throughout the specification and claims by either one or three-letter codes, as is commonly known in the art. When there is no indication, the L stereoisomer was used. The D isomers are indicated by "D" or "(D)" before the residue abbreviation.

As used herein, an "amino acid residue" means the moiety which remains after the amino acid has been conjugated to additional amino acid(s) to form a peptide, or to a moiety (such as a permeability-enhancing moiety), typically through the alpha-amino and carboxyl of the amino acid.

The terms "peptide of the invention", "synthetic peptide of the invention" and "modified peptide of the invention" all refer to peptides with a protecting group attached to the side chain of Arg (and optionally additional chemical modifications, including N- and C-terminal modifications). The terms refer to artificial, non-naturally occurring peptides, typically produced by standard peptide synthesis methods known in the art such as solid-phase peptide synthesis (SPPS). In some embodiments, a peptide of the present invention comprises additional side-chain modifications, on amino acids in the peptide in addition to Arg. In some embodiments, a peptide of the invention comprises side-chain protecting groups on amino acids in the peptide in addition to Arg. Such peptides are included provided that the anti-tumor activity is maintained.

According to some embodiments, the peptide of the invention is of 9-29 amino acids, 9-28 amino acids, 9-27 amino acids, 9-26 amino acids, 9-25 amino acids, 9-24 amino acids, 9-23 amino acids, 9-22 amino acids, 9-21 amino acids, 9-20 amino acids, 9-19 amino acids, 9-18 amino acids, 9-17 amino acids, 9-16 amino acids, 9-15 amino acids, 9-14 amino acids, 9-13 amino acids, 9-12 amino acids, 9-11 amino acids, 9-10 amino acids, or 9 amino acids. Each possibility represents a separate embodiment of the invention.

The term chemically modified", when referring to an amino acid, refers to an amino acid that is modified by one or more chemical modifications, which can be performed by techniques known in the art. Chemical modifications of amino acids encompass the side chain protecting groups noted above, and also encompass, but not limited to, acetylation, acylation, amidation, ADP-ribosylation, glycosylation, glycosaminoglycanation, methylation (e.g. N-methylation), myristoylation, pegylation, prenylation, phosphorylation, ubiquitination, and the like.

Analogs of the peptides are also within the scope of the present invention. As used herein, "analogs" are peptides which have the amino acid sequence according to the invention except for one or more amino acid changes, typically, conservative amino acid substitutions. In some embodiments, an analog has at least about 75% identity to the sequence of the peptide of the invention, for example at least about 80%, at least about 85%, at least about 90%, at least about 99% identity to the sequence of the peptide of the invention. Each possibility represents a separate embodiment of the present invention. Analogs are included in the invention as long as they remain pharmaceutically acceptable and their activity is not damaged.

Conservative substitutions of amino acids as known to those skilled in the art are within the scope of the present invention. Conservative amino acid substitutions include replacement of one amino acid with another having the same type of functional group or side chain e.g. aliphatic, aromatic, positively charged, negatively charged. Conservative substitution tables providing functionally similar amino acids are well known in the art.

The following is an example of classification of the amino acids into six groups, each contains amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K), Histidine (H);
5) Isoleucine (I), Leucine (L), Methionine (M), Valine (V); and
6) Phenylalanine (F), Tyrosine (Y), Tryptophan (W).

Analogs according to the present invention may comprise also peptidomimetics. "Peptidomimetics" refers to synthetic molecules containing non-peptidic structural elements that are capable of mimicking the biological action(s) of a natural parent peptide.

The peptides of the present invention are typically utilized in a linear form, although it will be appreciated that in cases where cyclization does not severely interfere with peptide characteristics, cyclic forms of the peptide can also be utilized. Cyclization of peptides may take place by any means known in the art, for example through free amino and carboxylic groups present in the peptide sequence, or through amino acids or moieties added for cyclization. Non limiting examples of cyclization types are: side chain to side chain cyclization, C-to-N terminal cyclization, side chain to terminal cyclization, and any type of backbone cyclization incorporating at least one Ni-w-substituted amino acid residue/s as described for example in WO 95/33765.

The present invention further provides conjugates comprising a peptide of the invention covalently linked to a moiety selected from the group consisting of a fatty acid, a polymer chain, an amino acid, a carrier or targeting peptide, a carrier or targeting protein, and a sugar moiety. Each possibility represents a separate embodiment of the present invention.

The term "conjugate" as used herein, refers to a product comprising the peptide of the invention covalently linked to a moiety e.g., a fatty acid, an amino acid, a protein, a sugar moiety, or a polymer chain. The moiety conjugated to the peptide of the invention can be attached to the N and/or C terminus of the peptide and/or to a side chain of an amino acid of the peptide. Each possibility represents a separate embodiment of the present invention.

According to some embodiments, the fatty acid used in the conjugate of the present invention is selected from the group consisting of saturated, unsaturated, monounsaturated and polyunsaturated fatty acids. According to some embodiments, the fatty acid is selected from the group consisting of decanoic acid, undecanoic acid, dodecanoic acid, myristic acid, palmitic acid, stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid. Each possibility represents a separate embodiment of the invention. According to additional embodiment the peptide is conjugated to a sphingolipid.

According to some embodiments, the polymer chain used in the conjugate of the present invention is a synthetic polymer selected from the group consisting of polyethylene glycol (PEG), polylactic acid, poly-L-lactic acid, poly-D,L-lactic acid, poly glycolic acid, poly-ε-caprolactone, poly-p-dioxanon, tri-methylene carbonate, poly anhydrides, poly ortho ester, poly urethanes, a poly amino acid, poly hydroxy alcanoate, poly phosphazene and poly-β-maleic acid. Each possibility represents a separate embodiment of the invention.

According to some embodiments, the peptide of the present invention as defined above is conjugated to an amino acid, peptide or protein, which functions as a carrier or targeting moiety of the peptide of the invention.

According to some embodiments, the carrier or targeting peptide that is conjugated to the peptide of the invention consists of 2-40 amino acids, for example 10-40 amino acids, or 10 amino acids. According to further embodiments, the carrier or targeting peptide consists of 10-20 amino acids.

According to some embodiments, the carrier or targeting protein that is conjugated to the peptide of the invention is a hormone, a growth factor or a cytokine. Each possibility represents a separate embodiment of the invention.

According to some embodiments, the amino acid, peptide, polypeptide, or protein comprises at least one amino acid in the D configuration.

In some embodiments, the peptide of the invention is covalently conjugated to a compound that improves cell permeability, e.g., a fatty acid. In other embodiments, the conjugate comprises a cell-penetrating peptide.

The term "fatty acid moiety" as used herein refers to a part of a fatty acid that exhibits a particular set of chemical and pharmacologic characteristics similar to the corresponding complete fatty acid origin molecule. The term further refers to any molecular species and/or molecular fragment comprising the acyl component of a fatty (carboxylic) acid.

The term "permeability" as used herein refers to the ability of an agent or substance to penetrate, pervade, or diffuse through a barrier or a membrane. The terms "cell permeability-", "cell-penetration-" and "permeability-enhancing-" moiety refers to any molecule known in the art which is able to facilitate or enhance penetration of molecules through membranes. Non-limitative examples include: hydrophobic moieties such as lipids, fatty acids, and bulky aromatic or aliphatic compounds; moieties which have cell-membrane receptors or carriers, such as steroids, vitamins, cytokines, growth hormones and the like, and amino acids such as methionine. Conjugation of a peptide of the invention to a permeability-enhancing moiety may be useful, for example, for local dermal administration of the peptide. Such modification may also be useful for systemic intradermal administration of the peptide.

According to some embodiments the hydrophobic moiety is selected from the group consisting of: phospholipids, steroids, sphingosines, ceramides, octyl-glycine, 2-cyclohexylalanine, benzolylphenylalanine, propionoyl (C3); butanoyl (C4); pentanoyl (C5); caproyl (C6); heptanoyl (C7); capryloyl (C8); nonanoyl (C9); capryl (C10); undecanoyl (C11); lauroyl (C12); tridecanoyl (C13); myristoyl (C14); pentadecanoyl (C15); palmitoyl (C16); phtanoyl ((CH3)4); heptadecanoyl (C17); stearoyl (C18); nonadecanoyl (C19); arachidoyl (C20); heniecosanoyl (C21); behenoyl (C22); trucisanoyl (C23); and lignoceroyl (C24).

Synthetic production of peptides is well known in the art. The peptides of the present invention can be synthesized using standard direct peptide synthesis (see, for example, Bodanszky, 1984, Principles of Peptide Synthesis, Springer-Verlag, Heidelberg), such as via solid-phase synthesis (see, for example, Merrifield, 1963, J. Am. Chem. Soc. 85:2149-2154). Examples of solid phase peptide synthesis methods include, but are not limited to, the BOC method, which utilizes tert-butyloxcarbonyl as the α-amino protecting group, and the FMOC method, which utilizes 9-fluorenyl-methyloxcarbonyl to protect the α-amino of the amino acid residues, both methods are well-known by those of skill in the art.

Alternatively, the peptides of the present invention can be synthesized using standard solution methods (see, for example, Bodanszky, M., Principles of Peptide Synthesis, Springer-Verlag, 1984).

The present invention also encompasses peptides in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, amides, methyl and ethyl esters or other types of esters or hydrazides.

The peptides of the present invention can contain one or more D-isomer forms of the amino acids. Production of retro-inverso D-amino acid peptides where at least one amino acid, and perhaps all amino acids, is D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

Pharmaceutical Compositions

The present invention provides according to some aspects a pharmaceutical composition comprising the peptide of the invention and a pharmaceutically acceptable carrier, excipient or diluent.

The term "pharmaceutical composition" as used herein refers to any composition comprising at least one pharmaceutically active ingredient, formulated such that it facilitates accessibility of the active ingredient to the target organ.

Carrier(s), excipient(s) and diluent(s) are "acceptable" in the sense of being compatible with the other ingredients of the composition and not deleterious to the recipient thereof. Suitable carriers typically include water, saline, oils, and polyols such as glycerol or propylene glycol.

The peptides may be formulated as neutral or salt forms. Pharmaceutically acceptable salts include the acid addition salts (formed with free amino groups) which are formed with inorganic acids such as hydrochloric or phosphoric acids, or with organic acids such as acetic, oxalic, tartaric and maleic. Salts formed with the free carboxyl groups may be derived from inorganic bases such as sodium, potassium, ammonium, calcium, or ferric hydroxides, or from organic bases such as isopropylamine, trimethylamine, 2-ethylamino ethanol, histidine and procaine.

The pharmaceutical compositions may be formulated for oral administration or for parenteral administration. For example, the pharmaceutical compositions may be formulated for injection administration, including but not limited to intravenous, intraarticular, intramuscular, subcutaneous or intradermal. Each possibility represents a separate embodiment of the present invention. Other routes of administration include inhalation, sublingual, rectal, dermal, transnasal and intranasal. Each possibility represents a separate embodiment of the present invention.

Thus, according to some embodiments, the pharmaceutical composition is for administration in a route of administration selected from the group consisting of oral, intraperitoneal, intravenous, intramuscular, subcutaneous, topical application, buccal, intradermal, transdermal, inhalation, sublingual, rectal, intravitreal, intravesicular, transnasal and intranasal. Each possibility represents a separate embodiment of the invention.

In some particular embodiments, the pharmaceutical composition is for administering orally. In additional particular embodiments, the pharmaceutical composition is for administering intravenously. In additional particular embodiments, the pharmaceutical composition is for administering intraperitoneally.

According to some embodiments, the pharmaceutical composition is formulated in a form selected from the group consisting of a solution, an emulsion, a suspension, a powder, a tablet, a capsule, a pill, a lozenge, a paste, a sustained-release formulation and the like. Each possibility represents a separate embodiment of the invention.

The compositions may be suitably formulated for intravenous, intramuscular, subcutaneous, or intraperitoneal administration and comprise sterile aqueous solutions of the peptides, which are preferably isotonic. Such formulations are typically prepared by dissolving solid active ingredient in water containing physiologically compatible substances such as sodium chloride, glycine, and the like, and having a buffered pH compatible with physiological conditions to produce an aqueous solution, and rendering said solution sterile. These may be prepared in unit or multi-dose containers, for example, sealed ampoules or vials.

In some embodiments, injectable solutions of the invention are formulated in physiologically compatible buffers such as Hank's solution, Ringer's solution, or physiological salt buffer.

The compositions may incorporate a stabilizer, such as for example polyethylene glycol, proteins, saccharides (for example trehalose), amino acids, inorganic acids, ethylenediamine tetraacetate (EDTA) disodium salt and admixtures thereof. Stabilizers are used in aqueous solutions at the appropriate concentration and pH. The pH of the aqueous solution is adjusted to be within the range of 5.0-9.0, preferably within the range of 6-8. For oral or sublingual the pH can be reduced. In formulating the peptides, anti-adsorption agent may be used. Other suitable excipients may typically include an antioxidant such as ascorbic acid.

The compositions of the invention may be formulated as controlled release preparations which may be achieved through the use of a polymer to complex or absorb the proteins. Appropriate polymers for controlled release formulations include, for example, polyester, polyamino acids, polyvinyl, pyrrolidone, poly (lactic acid), ethylenevinylacetate, ethylene vinylacetate copolymers, and cellulose derivatives such as methylcellulose. Alternatively, it is possible to entrap the peptides of the invention in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, macroemulsions, and nanoparticles.

In some embodiments, the compositions of the invention may be formulated for peroral or oral compositions in liquid solutions, emulsions, suspensions, and the like. The pharmaceutically-acceptable carriers suitable for preparation of such compositions are well known in the art. Peptides that are orally administered need to be protected as to avoid digestion by the gastrointestinal system.

The peptides of the invention can be coated with enteric coating layer(s) as to protect them from digestion. Enteric coating layer(s) may be applied using standard coating techniques. The enteric coating materials may be dissolved or dispersed in organic or aqueous solvents and may include one or more of the following materials: methacrylic acid copolymers, shellac, hydroxypropylmethcellulose phthalate, polyvinyl acetate phthalate, hydroxypropylmethylcellulose trimellitate, carboxymethylethyl-cellulose, cellulose acetate phthalate or other suitable enteric coating polymer(s). The pH at which the enteric coat will dissolve can be controlled by the polymers, combination and ratio of selected polymers, and/or their side groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

In some embodiments, the preparations described herein are formulated for parenteral administration, e.g., by bolus injection or continuous infusion. In some embodiments, compositions are suspensions, solutions or emulsions in oily or aqueous vehicles, and contain formulatory agents such as suspending, stabilizing and/or dispersing agents.

Uses of the Peptides

The present invention provides according to some aspects a method of treating cancer in a subject in need thereof, the method comprising administering to the subject a pharmaceutical composition comprising a therapeutically effective amount of a peptide of the invention and a pharmaceutically acceptable carrier, excipient or diluent.

According to an additional aspect, the present invention provides the use of a peptide of the invention in the manufacture/preparation of a medicament for treating cancer.

Without being bound by any particular theory or mechanism of action, the inhibitory effect of the peptides of the invention on tumor growth and tumor metastasis may be attributed to an augmenting effect on the immune system, which is required in various pathologies, such as cancer. The peptides of the invention may therefore be utilized in cell therapy, where cells of the immune system are contacted with the peptide ex-vivo to enhance their anti-tumor activity, and then infused to a subject in need thereof.

In some embodiments, the immune cells are autologous. According to these embodiments, immune cells are collected from a subject in need of treatment, contacted ex-vivo with the peptide of the invention, and then re-infused back to the subject. In other embodiments, the immune cells are allogeneic. According to these embodiments, immune cells are collected from a donor, treated in vitro with the peptide of the invention, and then infused into a subject in need thereof.

In some embodiments, the ex vivo treatment induces at least one of expansion, proliferation, activation, and/or abolishes and neutralizes deactivation of the immune cells.

In some embodiments, the immune cells are peripheral blood mononuclear cells (PBMC). In some particular embodiments, the immune cells are lymphocytes. In some exemplary embodiments, the lymphocytes are T cells. The T cells may be activated by a mitogen prior to re-infusion to the subject. In other embodiments, the T cells undergo antigen-specific activation prior to reinfusion to the subject.

Thus, according to a further aspect the present invention provides a method of treating cancer in a subject in need thereof, the method comprising: (i) incubating immune cells collected from the subject with a peptide of the invention as defined above; and (ii) re-infusing said immune cells to said subject.

In some embodiments, a method for enhancing anti-tumor activity of immune cells is provided, the method comprising ex-vivo incubating the immune cells with a peptide of the invention as defined above.

As referred to herein, the term "treating" is directed to ameliorating symptoms associated with a disease, and lessening the severity or cure the disease. In some embodiments, treating results in a reduction in tumor size. In additional embodiments, treating results in the decrease of tumor growth, decrease in tumor progression to a more advanced stage and/or decrease or inhibition of tumor metastasis. Treatment according to the present invention may also encompass prophylactic treatment. Prophylactic treatment may include prevention of tumor development (e.g., in subjects at risk of developing a particular type of cancer) and also prevention of tumor recurrence following treatment. In some embodiments, the subject to be treated using the methods of the present invention has undergone cancer treatment and displays no symptoms or signs of disease. For example, the subject may have no detectable tumors concomitant with normal levels of the markers of the subject's particular disease. In some embodiments, the subject is a subject with minimal residual disease. According to some embodiments, treatment of cancer according to the present invention includes treatment of pre-cancerous conditions.

The term "therapeutically effective amount" as used herein refers to an amount of the peptide of the present invention that is sufficient to reduce, decrease, and/or inhibit a disease, disorder or condition in an individual.

In some embodiments, the cancer is selected from the group consisting of: adrenocortical carcinoma, anal cancer, bladder cancer, brain tumor, brain stem glioma, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, laryngeal cancer, leukemia, acute lymphoblastic, leukemia, oral cavity cancer, liver cancer, lung cancer, small cell lymphoma, AIDS-related lymphoma, central nervous system (primary) lymphoma, cutaneous T-cell lymphoma, hodgkin's disease, non-hodgkin's disease, malignant mesothelioma, melanoma, merkel cell carcinoma, metasatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, sezary syndrome, skin cancer, cutaneous T-cell lymphoma, kaposi's sarcoma, melanoma, small intestine cancer, soft tissue sarcoma, testicular cancer, thymoma, malignant, thyroid cancer, urethral cancer, uterine cancer, sarcoma, vaginal cancer, vulvar cancer, and wilms' tumor. Each possibility represents a separate embodiment of the invention.

In some embodiments, the cancer is selected from the group consisting of breast cancer, skin cancer, and lung cancer. Each possibility represents a separate embodiment of the invention.

In some embodiments, the subject is a mammal, typically a human. In some embodiments, the subject is a mammal animal.

The peptides of the invention may be administered by any suitable administration route, selected from oral, topical, transdermal or parenteral administration. According to some embodiments, the route of administration is via topical application selected from dermal, vaginal, rectal, inhalation, intranasal, ocular, transnasal, auricular, sublingual and buccal. According to some embodiments, the route of administration is via parenteral injection. In various embodiments, the step of administering is carried out by a parenteral route selected from the group consisting of intravenous, intramuscular, subcutaneous, intradermal, intraperitoneal, intraarterial, intracerebral, intracerebroventricular, intraosseus and intrathecal. For example, the peptides can be administered systemically, for example, by parenteral routes, such as, intraperitoneal (i.p.), intravenous (i.v.), subcutaneous (s.c.), or intramuscular (i.m.) routes. The peptides of the invention and/or any optional additional agent may be administered systemically, for example, by intranasal and transnasal administration. The peptides of the invention and/or any optional additional agent may be administered locally.

Exemplary effective doses of the peptides of the invention are demonstrated hereinbelow in mice. A person of ordinary skill in the art will be able to determine an equivalent dose in human or other non-human mammals using known standard factors and calculations for converting doses.

In some embodiments, the peptides are administered at a dose ranging from about 0.1 ng/kg to about 20 mg/kg of the subject weight. In some embodiments, the peptides of the invention are administered at a dose ranging from about 20 ng/kg to about 100 ng/kg of the subject weight. In other embodiments, the peptide of the invention is administered at a dose ranging from about 0.1 mg/kg to about 10 mg/kg of the subject weight. In yet other embodiments, the peptide of the invention is administered at a dose ranging from 0.1, 1, 10, 20, 30, 50, 100, 200, 400, 500, 700, 900 or 1000 ng/kg of the subject weight, to about 100, 200, 400, 500, 700, 900, 1000, 1200, 1400, 1700, or 2000 ng/kg of the subject weight. Each possibility represents a separate embodiment of the invention. In yet other embodiments, the peptide of the invention is administered at a dose ranging from about 0.01, 0.05, 0.1, 0.5, 0.7, 1, or 2 mg/kg of the subject weight, to about 0.05, 0.1, 0.5, 0.7, 1, 2, 5, 10, 15, 20, 50, 100, 250, or 500 mg/kg of the subject weight. Each possibility represents a separate embodiment of the invention.

According to some embodiments, the peptide is parenterally administered at a dose ranging from about 10 ng/kg to about 100 µg/kg of the subject weight. According to certain embodiments, the peptide is parenterally administered at a dose ranging from about 10 ng/kg to about 1 µg/kg of the subject weight.

According to some embodiments, the peptide is orally administered at a dose ranging from about 0.001 mg/kg to about 500 mg/kg of the subject weight, for example from about 0.1 mg/kg to about 500 mg/kg of the subject's body weight.

According to some embodiments, the pharmaceutical composition is administered at least once a day. According to certain embodiments, the pharmaceutical composition is administered at least twice a week.

According to some embodiments, the pharmaceutical composition is administered every day for at least one week, alternatively the pharmaceutical composition is administered every day for at least one month, or further alternatively the pharmaceutical composition is administered every day until the tumor is eradicated.

In some embodiments, where the pharmaceutical composition is used for preventing recurrence of cancer, the pharmaceutical composition may be administered regularly for prolonged periods of time, according to instructions from a clinician.

As used herein the term "about" in reference to a numerical value stated herein is to be understood as the stated value+/−10%, more preferably +/−5%, even more preferably +/−1%, and still more preferably +/−0.1% from the specified value.

In some cases it may be advantageous to administer a large loading dose followed by periodic (e.g., weekly) maintenance doses over the treatment period. The peptides can also be delivered by slow-release delivery systems, pumps, and other known delivery systems for continuous infusion. Dosing regimens may be varied to provide the desired circulating levels of a particular peptide based on its pharmacokinetics. Thus, doses are calculated so that the desired circulating level of a therapeutic agent is maintained.

Typically, the effective dose is determined by the activity of the peptide and the condition of the subject, as well as the body weight or surface area of the subject to be treated. The dose and the dosing regime are also determined by the existence, nature, and extent of any adverse side effects that accompany the administration of the peptide in the particular subject.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Effect of YHI1 on Tumor Growth in Footpads of Mice Injected with Lung Tumor Cells YHI1 was synthesized by solid phase synthesis to over 95% purity. To assess the effect of YHI1 on local tumor growth, lung cancer cells were injected into footpads of mice to induce the formation of a topical tumor, and the tumor size was measured in mice treated with several dosages of YHI1 or with vehicle only. Two separate experiments were carried out using this model, one in which YHI1 and vehicle were administered orally and another in which YHI1 and vehicle were administered via intraperitoneal (i.p.) injection.

Oral Administration of YHI1:
Experimental Procedure:

Female C57BL/6 mice were injected in the footpads with D122 cells ($2 \times 10^5$ cells per mouse suspended in 50 µl PBS), a highly metastatic 3LL Lewis lung carcinoma. YHI1 (dissolved in saline) was orally administered at the indicated doses 8, 6, 4 and 1 day prior to cell injection and thereafter during 35 days, 3 times a week. Control mice received the vehicle (saline). Tumor size (diameter) was measured by a caliper. Baseline value (before cell injection) was subtracted from each measurement. Groups: control (n=10), and YHI1—0.1 mg/kg (n=9), 1 mg/kg (n=10), 5 mg/kg (n=8).

Results:

FIG. 1A shows that orally administered YHI1 reduced the rate of tumor growth. The highest dose, 5 mg/kg body weight, was more effective in reducing tumor size than the lower doses of 1 mg/kg and 0.1 mg/kg body weight. The results are expressed as mean±SE. $p<0.05$ for 5 mg/kg group versus control, for the period of 23-35 days (Mann-Whitney test).

Intraperitoneal Administration of YHI1:
Experimental Procedure:

Female C57BL/6 mice were injected in the footpads with D122 cells ($2 \times 10^5$ cells per mouse suspended in 50 µl PBS). YHI1 was i.p. administered at the indicated doses 8, 6, 4 or 1 day prior to cell injection and thereafter up to 34 days, 3 times a week. Control mice received the vehicle (saline). Tumor size (diameter) was measured by a caliper. Baseline value (before cell injection) was subtracted from each measurement. Groups: control (n=10), and YHI1—0.1 µg/kg (n=10), 1 µg/kg (n=10), 10 µg/kg (n=11), 100 µg/kg (n=9).

Figure 1B:
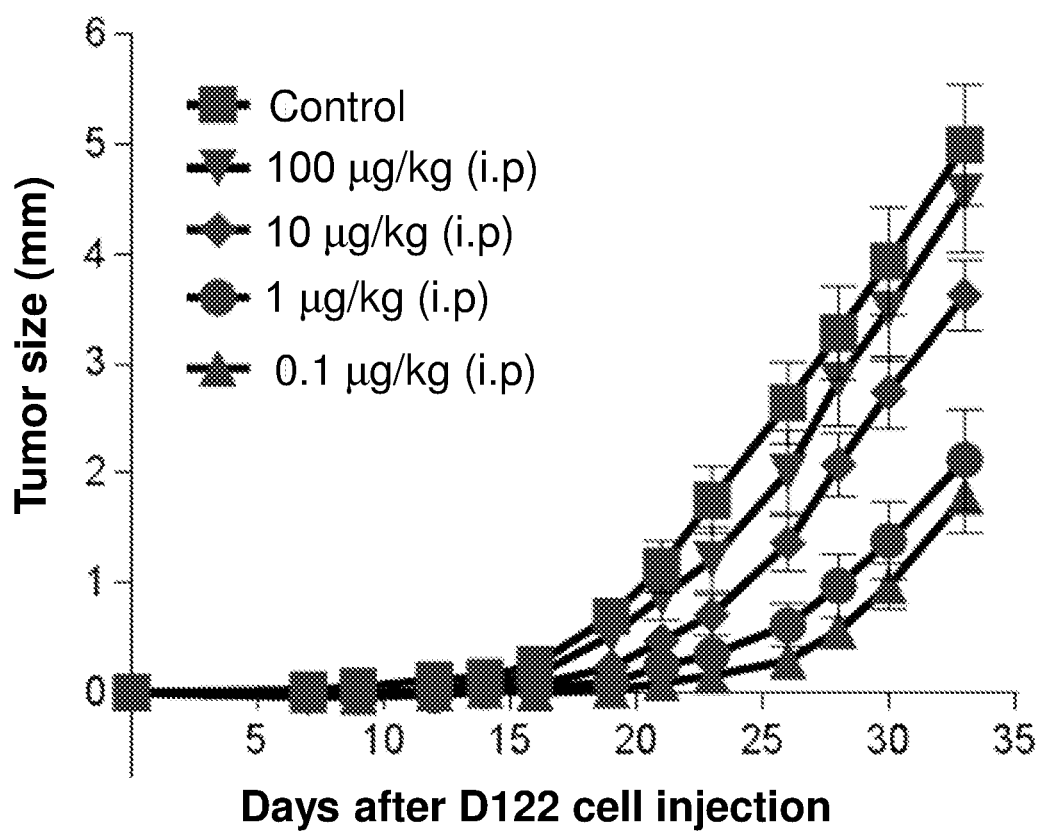

Results:

FIG. 1B shows that similar to oral administration, i.p. administered YHI1 reduced the rate of tumor growth. Interestingly, i.p. administration resulted in a different pattern where the highest activity was obtained with the lowest dose: YHI1 administered intraperitoneally at a dose of 0.1 µg/kg was more effective in reducing tumor size than higher doses of YHI1 (up to 100 µg/kg body weight).

The results are expressed as mean±SE using the Kruskal-Wallis test and Dunnett's multiple comparison post test for statistical evaluation of the differences between the treated groups and control group at each time point.

$p<0.001$ and $p<0.01$ for 0.1 µg/kg group versus control and 1 µg/kg group versus control, respectively, for the period of 19-33 days;

$p<0.001$ and $p<0.05$ for 0.1 µg/kg and 1 µg/kg groups, respectively, for the period of 16-33 days.

Example 2

Effect of YHI1 on Lung Metastasis Formation in a Mouse Model of Lung Metastasis

To examine the effect of YHI1 on cancer cell metastasis, lung metastasis was induced in mice, and the lung weight and the number of large metastases in mice treated with YHI1 or with vehicle only were measured.

Experimental Procedure:

Female C57BL/6 mice were i.v. injected with D122 cells ($5\times10^5$ cells per mouse suspended in 100 µl PBS). YHI1 was i.p. administered at doses of 0.1 µg/kg body weight and 0.01 µg/kg body weight 8, 6, 4 and 1 day prior to cell injection and thereafter up to 35 days, 3 times a week. Control mice received the vehicle (saline).

Lung Weight:

Lung weight was determined on day 35 for each animal. Mean weight of lungs of healthy-non injected mice was subtracted from each value of the experimental and control groups, and the results are expressed as Δ lung weight. n=11, 10 and 9 mice for control, YHI1 0.1 and 0.01 µg/kg groups, respectively. Results are expressed as mean±SE using the Kruskal-Wallis test and Dunnett's multiple comparison post test for statistical evaluation of the differences in lung weight between the experimental groups and control mice. *$p<0.05$ for both 0.1 µg/kg and 0.01 µg/kg groups.

Figure 2:
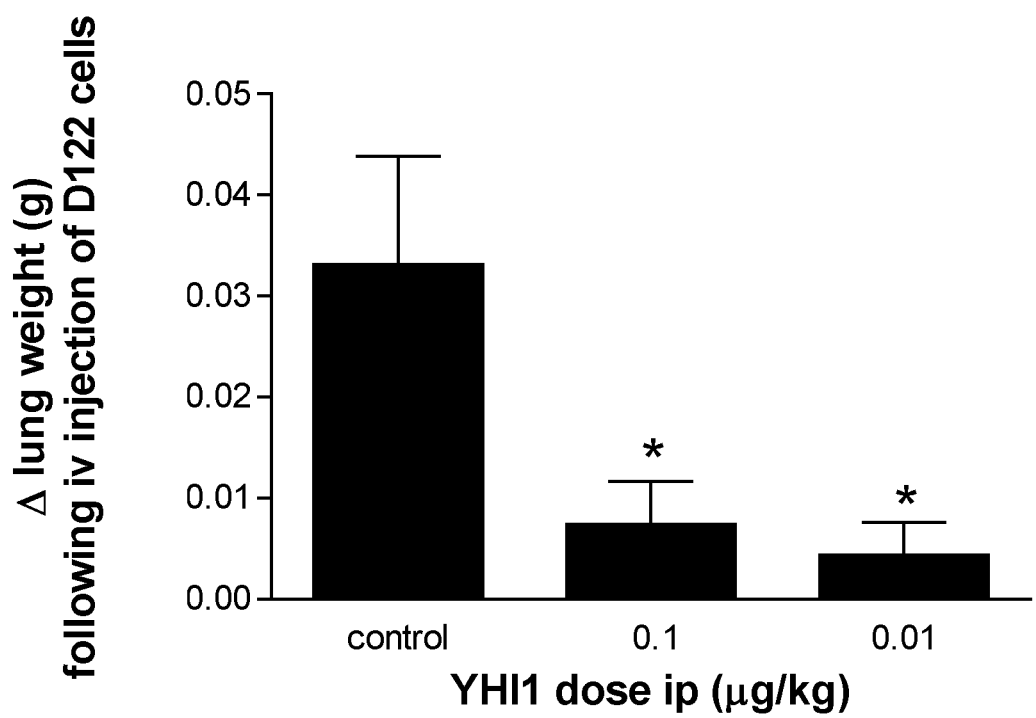
FIG. 2 shows the effect of YHI1 on lung metastasis in mice inoculated with lung tumor cells, measured as a change in lung weight. Female C57BL/6 mice were intravenously (i.v) injected with D122 cells ($5 \times 10^5$ cells). YHI1 was i.p. administered 8, 6, 4 and 1 day prior to tumor cell injection at doses of 0.1 μg/kg body weight and 0.01 μg/kg body weight and thereafter up to 35 days, 3 times a week. Control mice received the vehicle (saline). Tumor progression was evaluated by measuring lung weight at the end of the experiment (on day 35) and subtracting lung weight of naïve animal from each value. *$p<0.05$ vs. control.

As shown in FIG. 2, YHI1 administered intraperitoneally at 0.1 or 0.01 µg/kg body weight significantly reduced the change in lung weight compared to control (78% and 87% reduction in Δ lung weight, respectively, $p<0.05$), indicating that YHI1, even at a dose of 0.01 µg/kg body weight was effective in diminishing lung metastasis.

Figure 3:
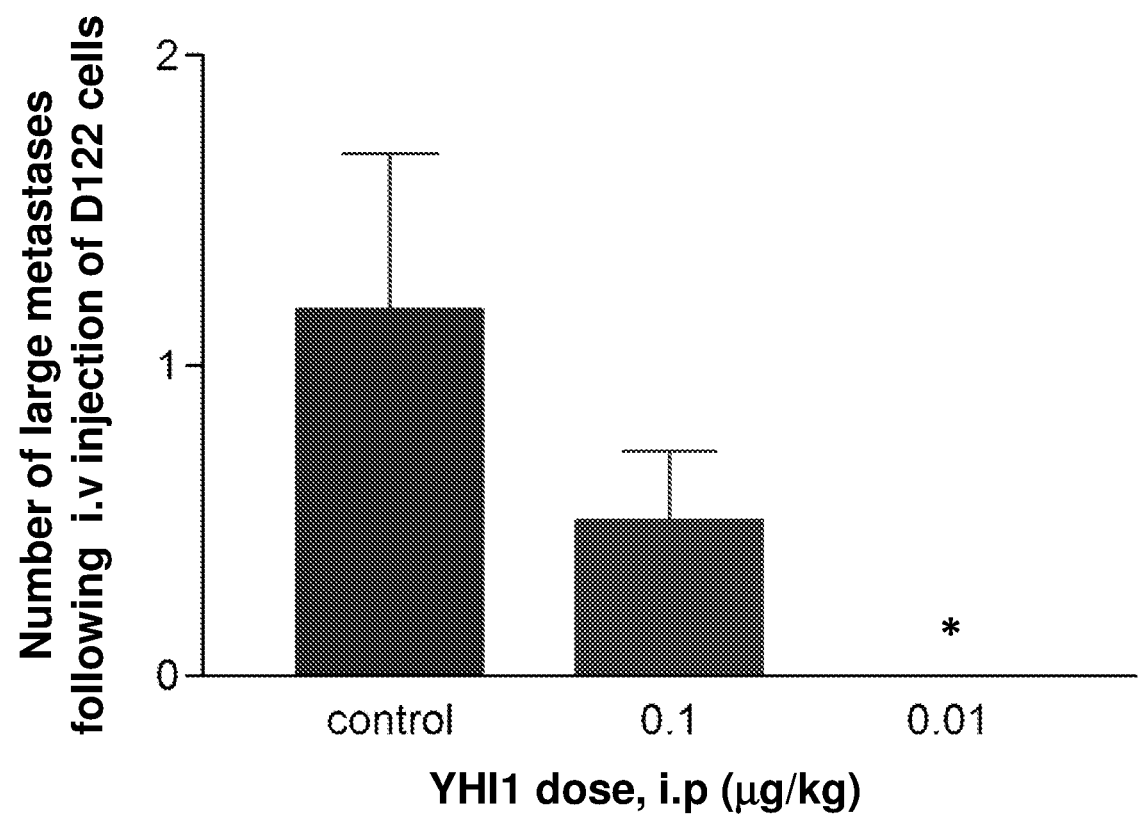
FIG. 3 shows the effect of YHI1 treatment on large metastases formation in the lung in mice inoculated with lung tumor cells, represented by the number of large metastases. Female C57BL/6 mice were i.v. injected with D122 cells ($5 \times 10^5$ cells). YHI1 was i.p. administered 8, 6, 4 and 1 day prior to cell injection at doses of 0.1 μg/kg body weight and 0.01 μg/kg body weight and thereafter up to 35 days, 3 times a week. Control mice received the vehicle (saline). The number of large metastases was quantified. *$p<0.05$.

Large Metastases:

The number of large visible metastases in the lungs was next quantified. As shown in FIG. 3, treatment with YHI1 at a dose of 0.1 µg/kg body weight reduced the number of large metastases by 58%, compared to control, and treatment with YHI1 at a dose of 0.01 µg/kg body weight totally eliminated visible metastases. The results are expressed as mean±SE. *$p<0.05$ Mann Whitney test.

Figure 4:
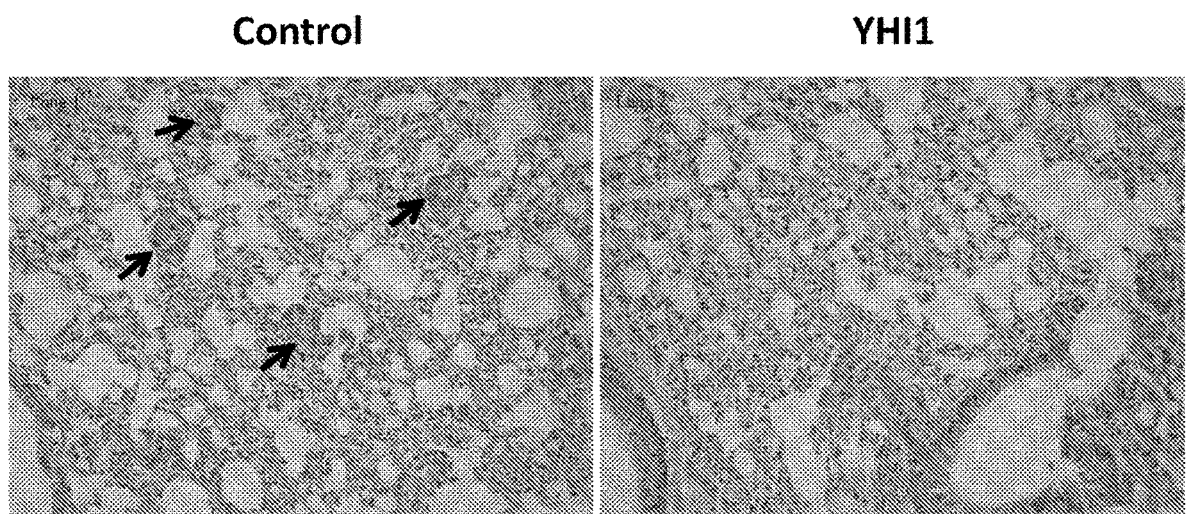
FIG. 4 shows representative photomicrographs of lung histological sections following YHI1 treatment in mice inoculated with lung tumor cells. Female C57BL/6 mice were i.v. injected with D122 cells. YHI1 at a dose of 0.01 μg/kg body weight was i.p. administered 8, 6, 4 and 1 day prior to tumor cell injection and thereafter up to 35 days, 3 times a week. Control mice received the vehicle (saline). Lungs were fixed, sectioned and stained with H&E. Arrows indicate micrometastases.

Histopathology:

The lungs were then fixed, sectioned and stained with H&E for histopathological evaluation. FIG. 4 shows representative micrographs of histological sections of the lung (control and YHI1—0.01 µg/kg treated mice). The histological evaluation correlated with the above finding: a control lung showed multiple micrometastases regions (marked with arrows) while that of a YHI1-treated animal was tumor free.

Example 3

Effect of YHI1 on Lung Metastasis in Mice Treated One Week after Cell Injection

To assess whether time of treatment affects the metastasis process, YHI1 was administered 7 days after tumor cell injection. Female C57BL/6 mice were i.v. injected with D122 cells ($5\times10^5$ cells per mouse suspended in 100 µl PBS). YHI1 was i.p. administered at a dose of 0.01 µg/kg body weight (volume of 0.1 ml) 7 days after cell injection and thereafter up to 35 days, 3 times a week. Control mice received the vehicle (saline). Lung weight, number of tumors, lung histology (H&E) and survival were determined on day 35 after cell inoculation for each animal Lung weight was compared to a healthy lung removed from a naïve animal.

Figure 5:
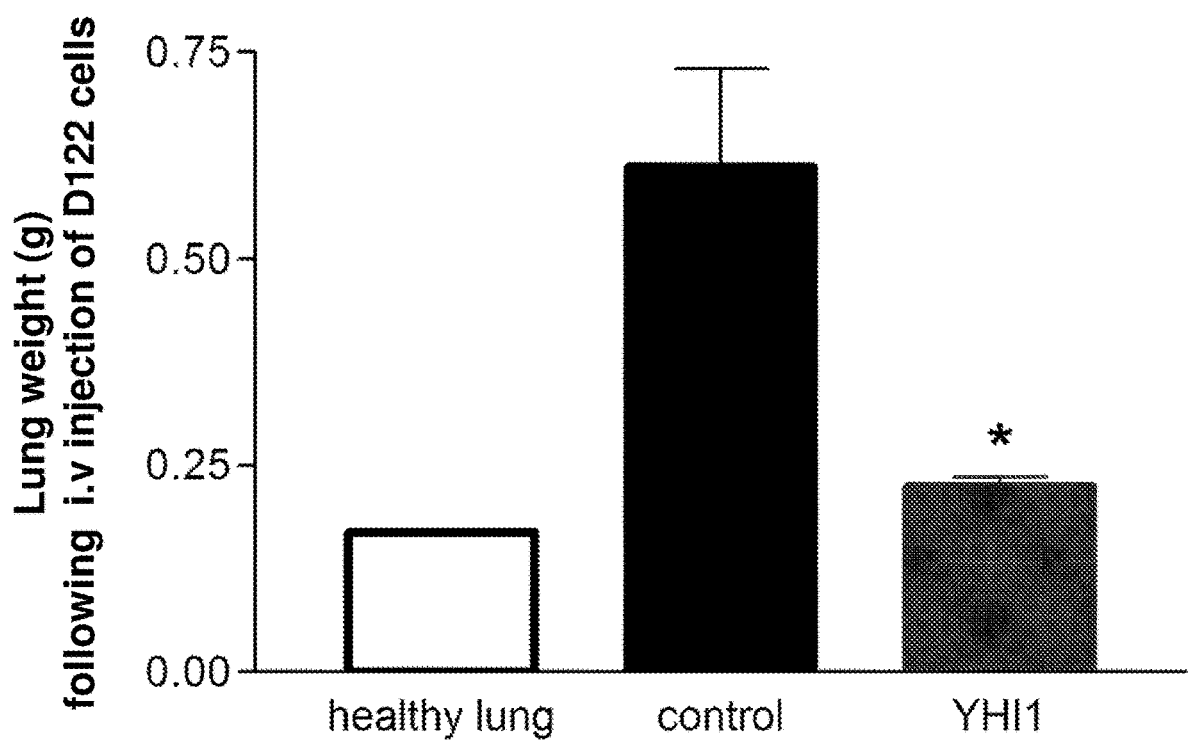
FIG. 5 shows the effect of YHI1 on lung metastasis in mice administered with YHI1 7 days after tumor cells injection, measured as a change in lung weight. Female C57BL/6 mice were i.v. injected with D122 cells. YHI1 was i.p. administered 7 days after cell injection at a dose of 0.01 μg/kg and thereafter up to 35 days, 3 times a week. Controls received the vehicle (saline). *$p=0.0052$ vs. control.

As shown in FIG. 5, the lung weight of mice treated with YHI1 was significantly lower than the lung weight of control mice (63% lower, $p=0.0052$), indicating that YHI1 reduced lung metastasis even when administered 7 days after tumor inoculation. The results are expressed as mean±SE.

Figure 6:
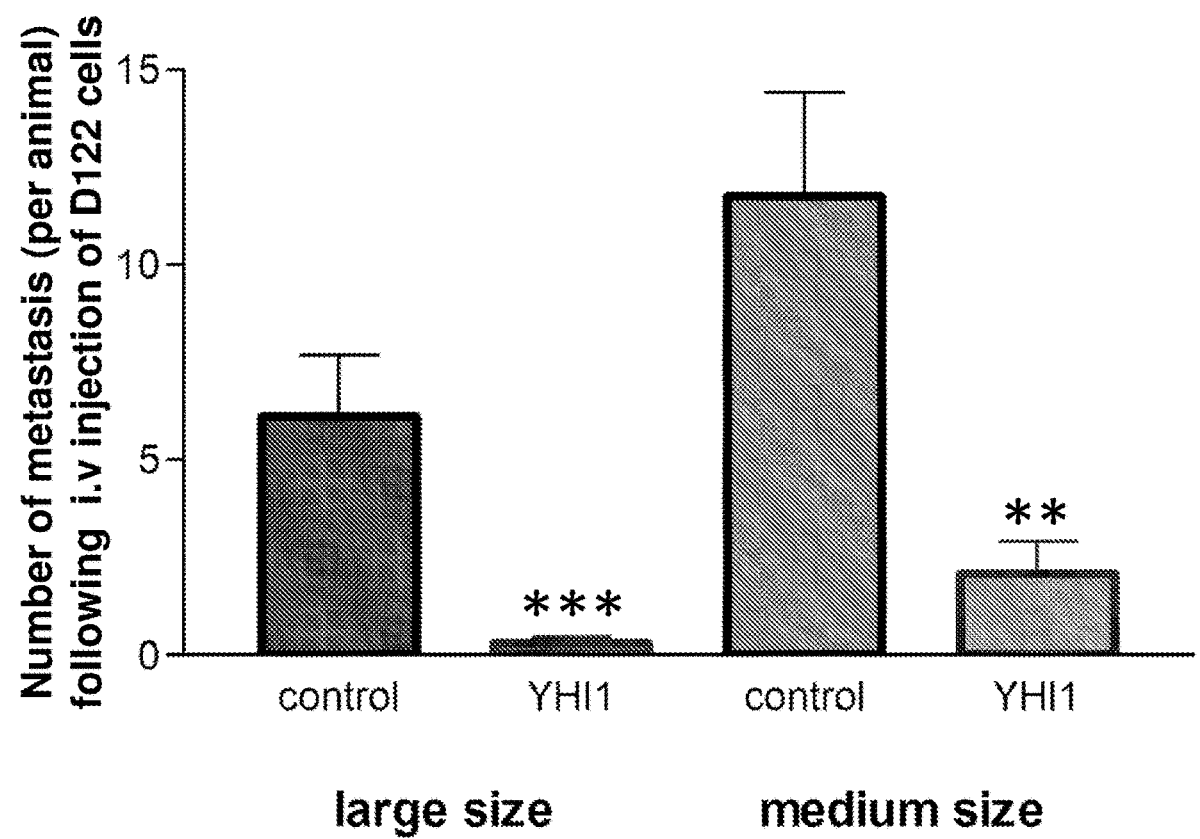
FIG. 6 shows the effect of YHI1 on lung metastasis (according to size) in mice administered with YHI1 7 days after tumor cells injection, represented by the number of large size and medium size metastases after 35 days of YHI1 treatment. Female C57BL/6 mice were i.v. injected with D122 cells. YHI1 was i.p. administered 7 days after tumor cell injection at a dose of 0.01 µg/kg and continued 3 times a week along the experiment. The experiment was terminated 35 days after cell injection. Controls received the vehicle (saline). p=0.0015, *p=0.0008.

The effect of YHI1 on metastasis was further evaluated by counting the number of large and medium sized metastases in the lungs. As shown in FIG. 6, the number of both large and medium sized metastases was significantly reduced upon treatment with YHI1 ($p=0.0015$, *$p=0.0008$). The results are expressed as mean±SE.

Figure 7:
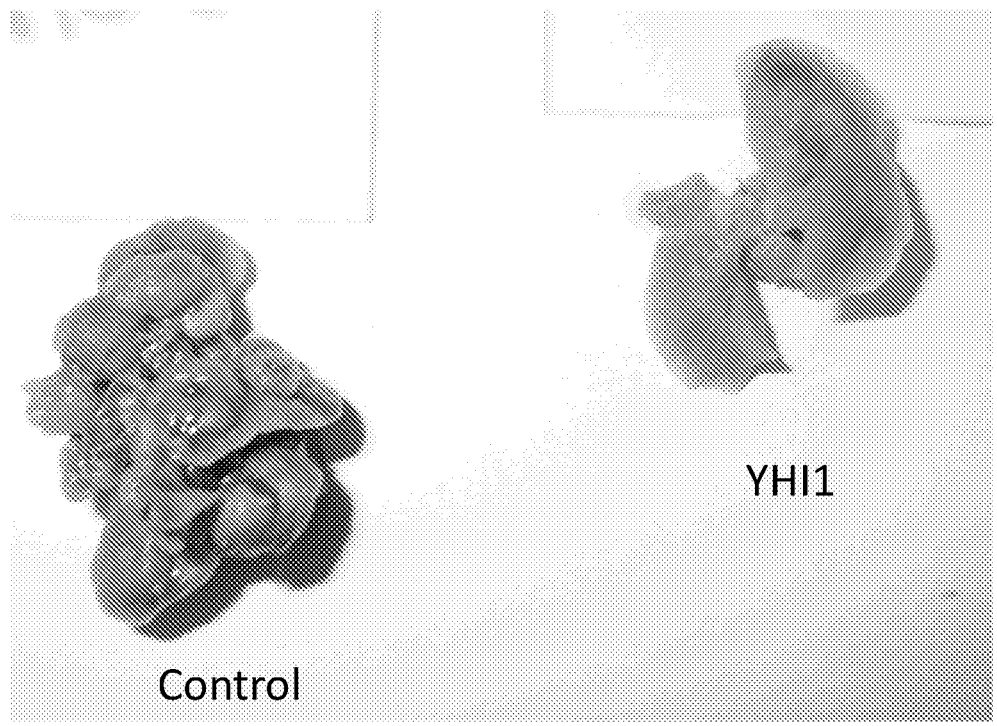
FIG. 7 shows representative photographs of a lung of YHI1-treated mouse and a lung of a control mouse inoculated with D122 cells. Female C57BL/6 mice were i.v. injected with D122 cells. YHI1 was i.p. administered 7 days after cell inoculation at a dose of 0.01 µg/kg body weight and thereafter up to 35 days, 3 times a week. Control mice received the vehicle (saline). Lungs were removed and photographed.
Figure 8A:
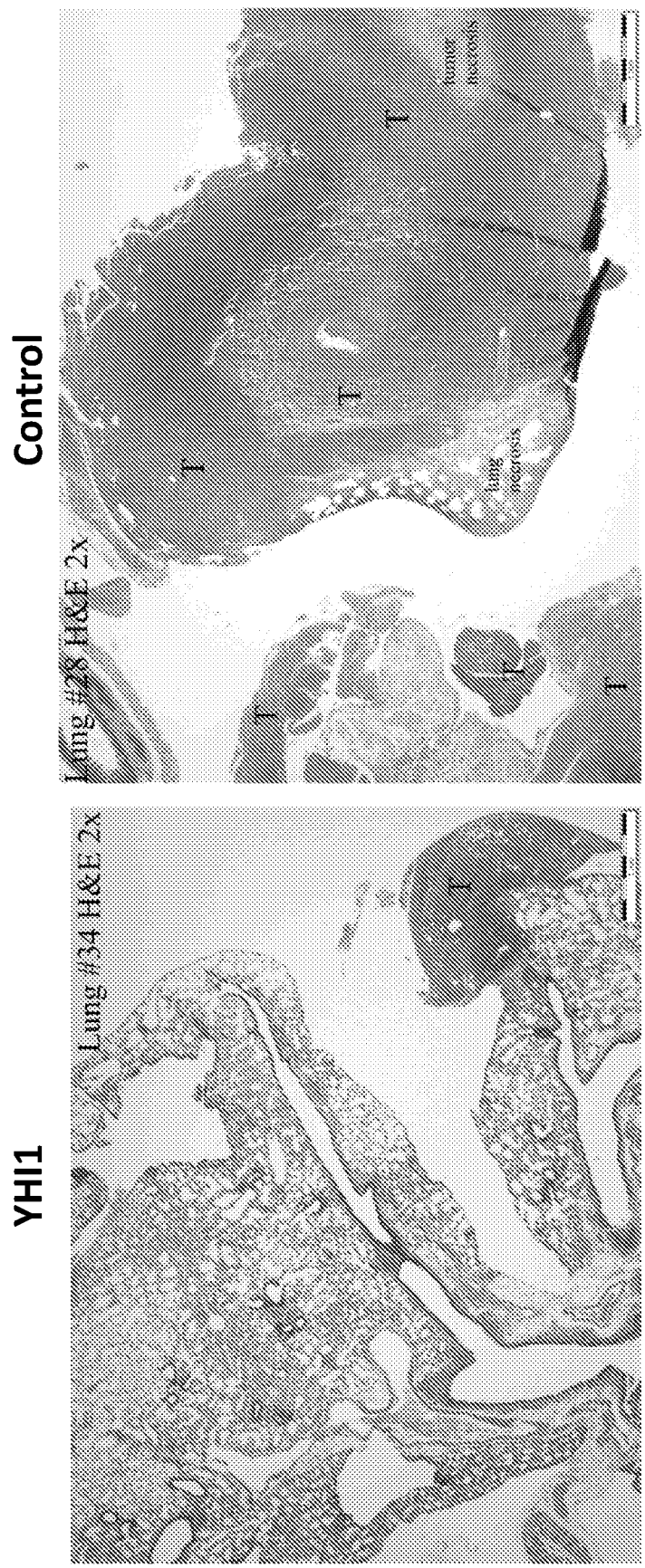
FIGS. 8A-8B show representative histological evaluations of a lung of a YHI1-treated mouse and a lung of a control mouse inoculated with D122 cells.
Figure 8B:
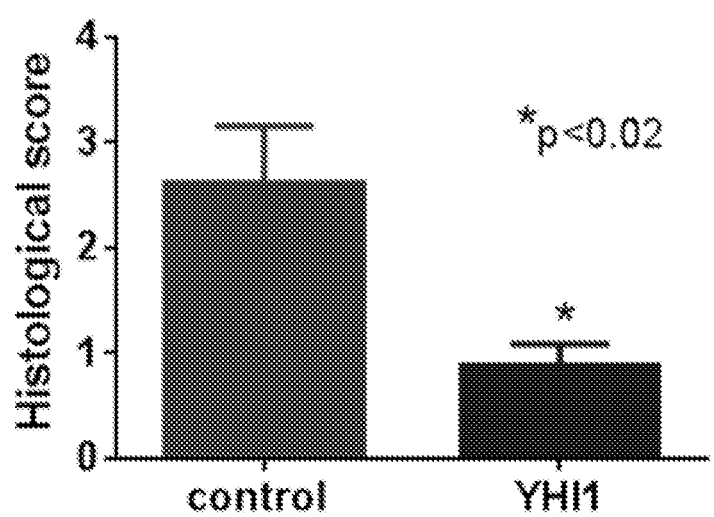

FIG. 7 shows representative photographs of a lung of a YHI1-treated mouse (right) and a lung of a control mouse (left). Evaluation of histological lung sections showed extensive infiltration of the lung parenchyma by the tumor (T) in the control lung, together with necrosis of the remaining un-infiltrated lung and central tumor necrosis (FIG. 8A, right panel). In contrast, only a single focus of viable tumor (T) was observed in the lung of YHI1-treated mouse, while the remaining lung tissue appeared normal (FIG. 8A, left panel). In addition, histological score of lung metastasis was high in the control lung and significantly reduced in the lung from a YHI1-treated mouse (FIG. 8B, results are expressed as mean±SE).

Figure 9:
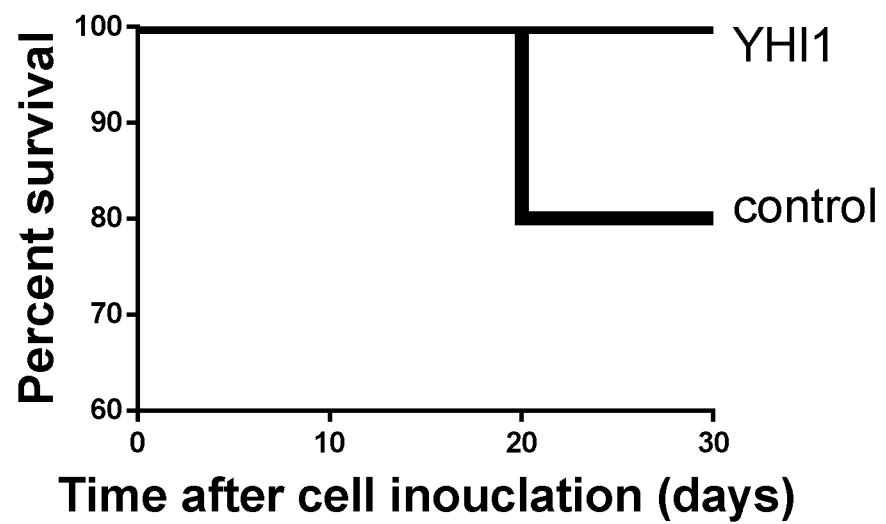
FIG. 9 shows the effect of YHI1 on survival of mice inoculated with D122 cells. Female C57BL/6 mice were i.v. injected with D122 cells. YHI1 was i.p. administered 7 days after cell inoculation at a dose of 0.01 µg/kg body weight and thereafter up to 35 days, 3 times a week. Control mice received the vehicle (saline).

With respect to survival, FIG. 9 shows that YHI1 improved survival of the D122-injected mice: full animal survival was observed in YHI1-treated group in contrast to only 80% survival in the control group.

Example 4

Effect of YHI1 on Lung Metastasis in Mice Inoculated with 4T1 Mammary Carcinoma Cells Female BALB/c mice (9-10 weeks) were i.v. injected with mammary 4T1 tumor cells ($1\times10^4$ cells in 0.2 ml culture medium). YHI1 was i.p. administered to the mice at doses of 3, 10 and 30 ng/kg body weight (0.1 ml) on day 5 after tumor cell inoculation and thereafter 6 days a week, until day 21, on which day the mice were sacrificed. Control mice received saline (vehicle) injections. Additional 3 mice remained naïve ("pure control", no cell injection, no treatment). Each dose group contained 10 mice. At the end of the experiments the mice were sacrificed, the lungs of the mice were removed, weighed and quantified for the number of foci.

Figure 10:
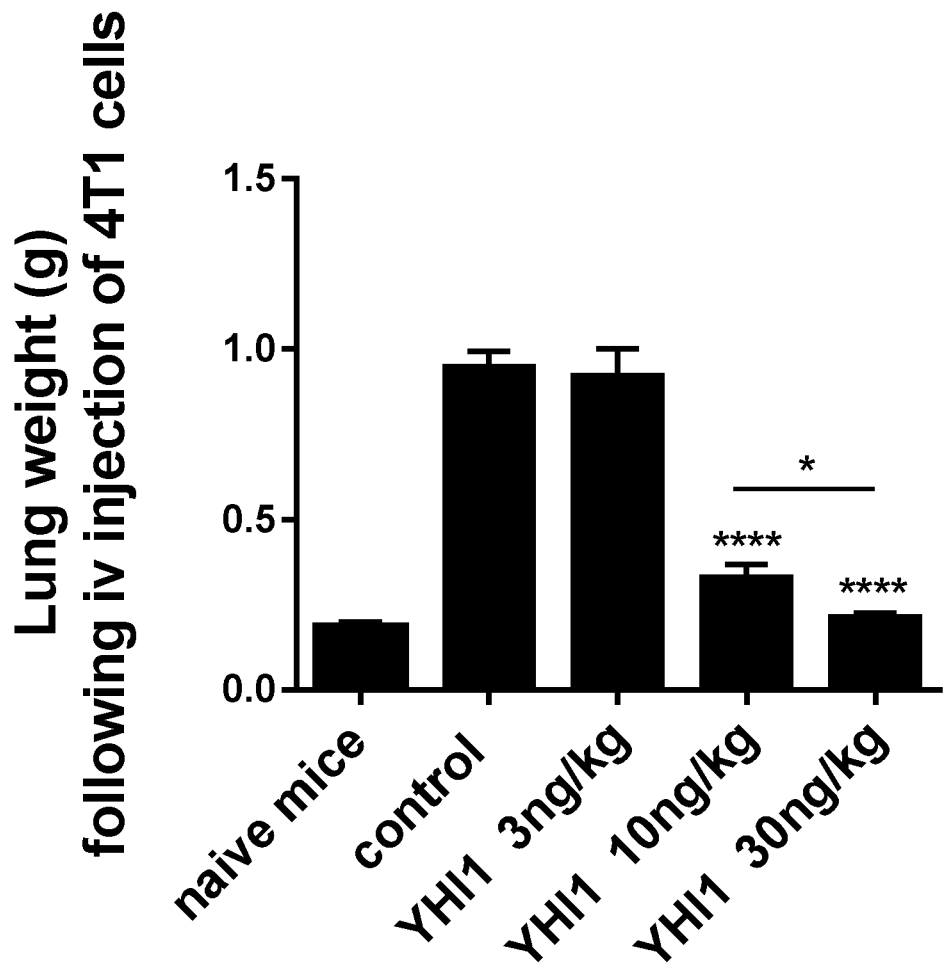
FIG. 10 shows the effect of YHI1 on lung metastasis in mice inoculated with 4T1 mammary carcinoma cells, measured as a change in lung weight. Female BALB/c mice were i.v. injected (tail vein) with mammary 4T1 tumor cells ($1 \times 10^4$ cells). YHI1 was i.p. administered 5 days after cell injection at doses of 3, 10 and 30 ng/kg body weight (0.1 ml), and thereafter 6 days a week until day 21. Controls received the vehicle (saline). Additional 3 mice remained naïve ("pure control", no cell injection, no treatment). ****p<0.0001 in comparison to control; *p<0.02 for comparison between 30 and 10 ng/kg YHI1.

As shown in FIG. 10, while YHI1 at a dose of 3 ng/kg body weight had no effect on lung weight, YHI1 at doses of 10 ng/kg and 30 ng/kg body weight significantly reduced the lung weight of mice (65% and 78%, respectively

Figure 11:
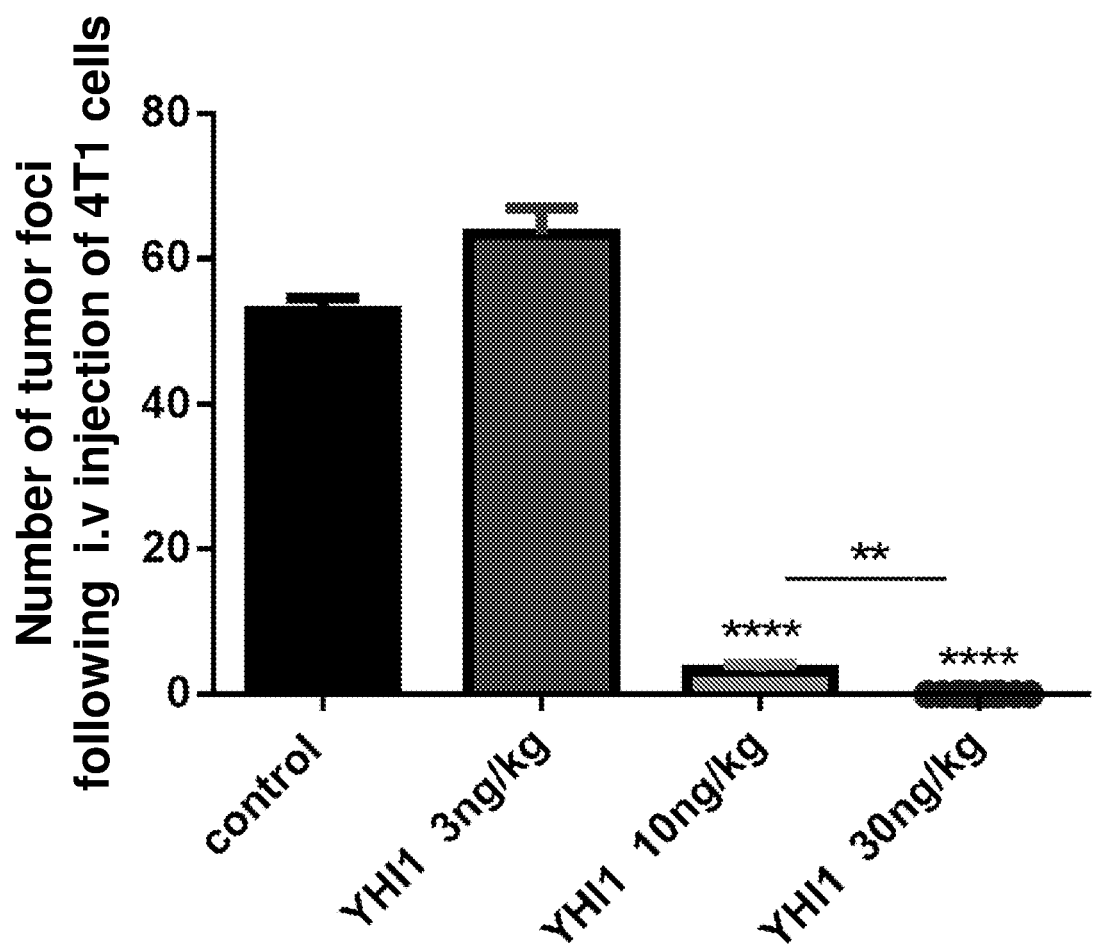
FIG. 11 shows the effect of YHI1 on lung metastasis in mice inoculated with 4T1 mammary carcinoma cells, represented by the number of lung foci. Female BALB/c mice were i.v. injected with 4T1 cells. YHI1 was i.p. administered starting 5 days after cell inoculation and thereafter 6 days a week until day 21. Lungs were removed and the number of tumor foci was quantified. **p<0.0001 in comparison to control; p<0.005 for comparison between YHI1 30 ng/kg body weight and YHI1 10 ng/kg body weight.

****p<0.0001 in comparison to control; *p<0.02 for comparison between 30 and 10 ng/kg YHI1 (student's t test). Results are expressed as mean±SE) Similarly, as shown in FIG. 11, while YHI1 at a dose of 3 ng/kg body weight had no effect on foci number, YHI1 at a dose of 10 ng/kg and 30 ng/kg body weight significantly reduced the number of foci (94% and 100% reduction, respectively, **p<0.0001 in comparison to control; p<0.005 for comparison between YHI1 30 ng/kg body weight and YHI1 10 ng/kg body weight (student's test). Results are expressed as mean±SE). The results indicate that YHI1 is highly effective in eradicating mammary tumor cell (4T1) lung metastasis.

Figure 12A:
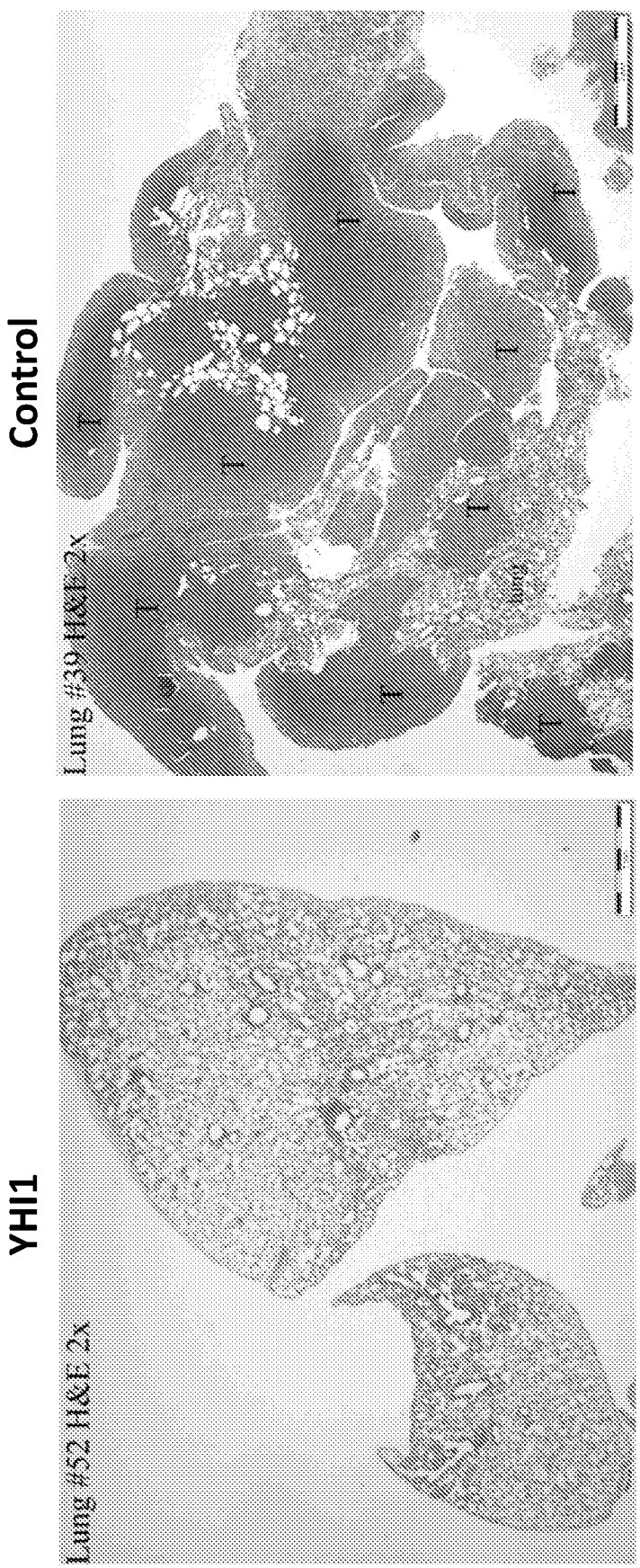
FIGS. 12A-12B show representative histological evaluations of a lung of a YHI1-treated mouse and a lung of a control mouse inoculated with 4T1 mammary carcinoma cells.
Figure 12B:
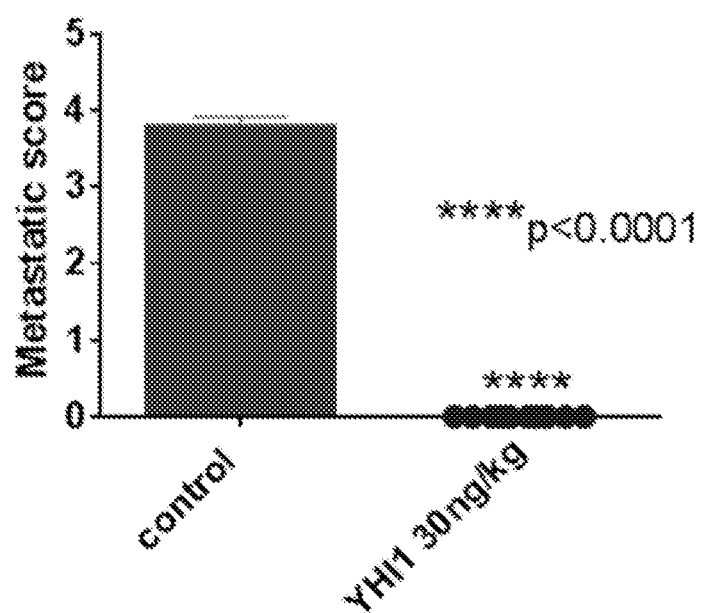

Evaluation of histological lung sections of a control lung versus a lung from a mouse treated with YHI1 30 ng/kg showed extensive infiltration of the lung parenchyma by the tumor (T) in the control lung, with almost no normal lung tissue observed (FIG. 12A, right panel). In contrast, normal lung tissue with no evidence of metastases was observed in the lung of a YHI1-treated mouse (FIG. 12A, left panel). In addition, histological score of lung metastasis was high in the control lungs and significantly reduced in the lungs from YHI1-treated mice (FIG. 12B and Table 1 below).

TABLE 1 histological scores of lungs from control vs. YHI1-treated mice

| Group | Specimen No. | Score | Description (blindly evaluated) |
|---|---|---|---|
| Control* | i | 4 | Multifocal coalescing areas of neoplastic proliferation involving approximately 80% of the lung parenchyma on section. The entire neoplastic tissue is viable. |
|  | Ii | 4 | Multifocal coalescing neoplastic foci involving approximately 75% of the parenchyma on section. There is approximately 10 to 15% of tumor necrosis. |
|  | Iii | 4 | Multifocal coalescing neoplastic foci involving approximately 75% of the lung parenchyma with complete collapse of the remaining non-neoplastic lung. There is extensive hemorrhage and necrosis of the tumor involving approximately 30% of the largest neoplastic area. |
|  | Iv | 4 | Multifocal coalescing neoplastic foci involving approximately 90% of the lung parenchyma with minimal necrosis of the neoplastic tissue. The viable lung is emphysematous. |
|  | V | 4 | Multifocal coalescing foci of neoplasia in the lung involving approximately 75% of the parenchyma with few small foci of necrosis involving less than 25% of the neoplastic tissue. |
|  | Vi | 3 | Multifocal coalescing neoplastic foci involving approximately 60% of the parenchyma with minimal necrosis. |
|  | Vii | 4 | Multifocal coalescing foci of neoplasia in the lung involving approximately 80% of the parenchyma with minimal necrosis of the neoplastic tissue. |
|  | Viii | 4 | Multifocal coalescing foci of neoplasia in the lung involving approximately 75 to 80% of the parenchyma with two small foci of necrosis of the neoplastic tissue. |
|  | Ix | 3 | Multifocal coalescing foci of neoplasia involving 50 to 60% of the parenchyma with many neoplastic emboli. There is minimal necrosis of the neoplastic tissue. |
| YHI 30 ng/kg | i | 0 | No metastases observed. |
|  | Ii | 0 | No metastases observed. |
|  | Iii | 0 | No metastases observed. |
|  | Iv | 0 | No metastases observed. |
|  | V | 0 | No metastases observed. |
|  | Vi | 0 | No metastases observed. |
|  | Vii | 0 | No metastases observed. |
|  | Viii | 0 | No metastases observed. |
|  | Ix | 0 | No metastases observed. |
|  | X | 0 | No metastases observed. |

*Nine specimens, one animal died before sacrificing the animals.

Example 5

Effect of YHI1 on Tumorigenicity of B16-F10 Cells

To examine the effect of YHI1 on melanoma tumor cells, female C57BL/6 mice (6-7 weeks) were subcutaneously injected in the lateral thoracic-abdominal area with B16-F10 cells ($2 \times 10^5$ cells in 0.1 ml culture medium). YHI1 was i.p. administered at doses of 30 and 100 ng/kg body weight (0.1 ml) on day 3 after tumor cell inoculation and thereafter until day 20 of tumor cell inoculation, 6 times a week. Control mice received saline (vehicle) injections. Each dose group contained 10 mice. Tumor size was measured along the experiment and was expressed as multiplication of length and width of the tumor.

Figure 13:
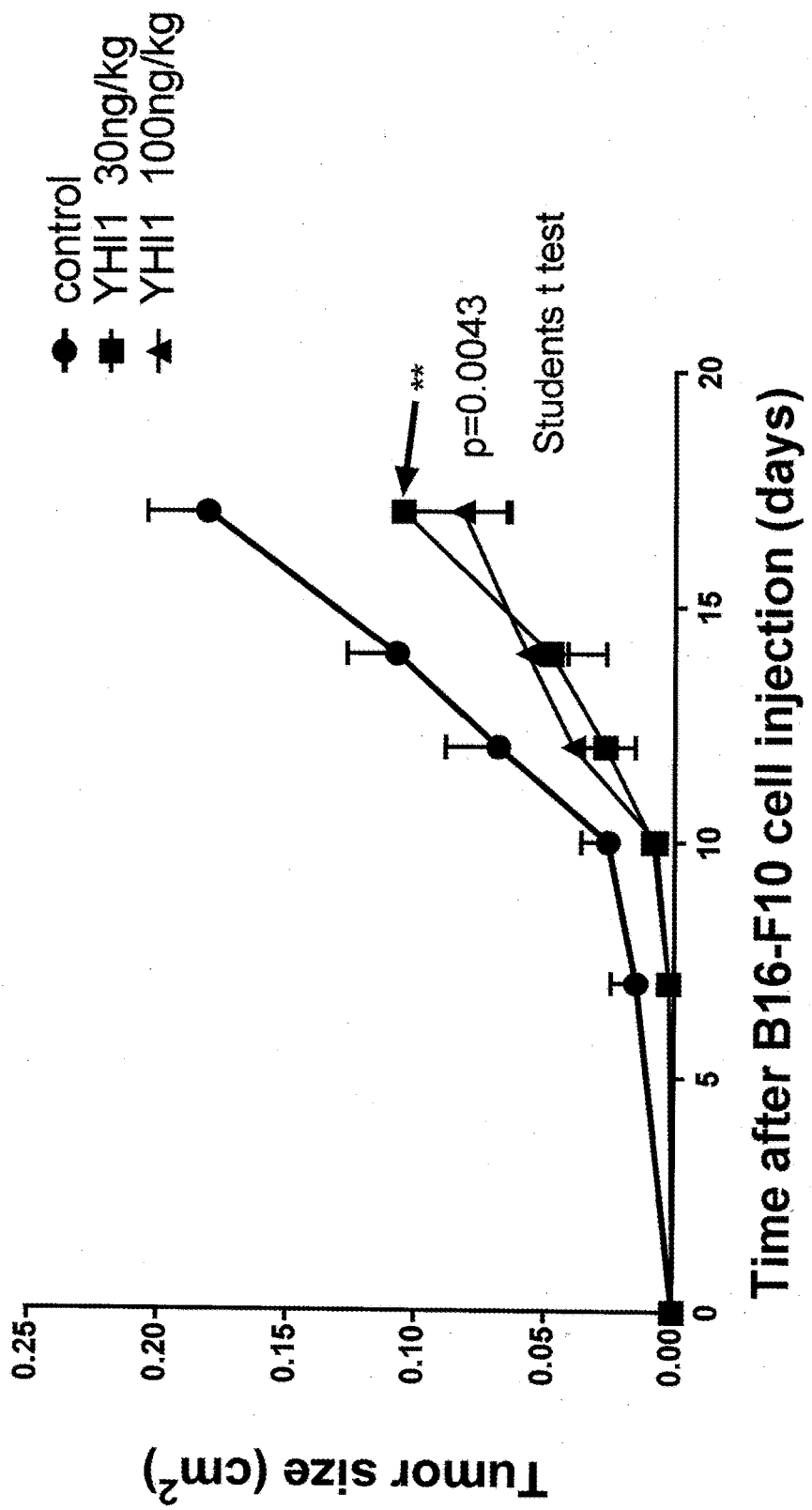
FIG. 13 shows the effect of YHI1 on tumorigenicity (size of a topical tumor) of B16-F10 melanoma cells. Female C57Bl/6 mice were subcutaneously injected in the lateral thoracic-abdominal area with B16-F10 cells. YHI1 was i.p. administered at the indicated doses starting 3 days after cell inoculation and thereafter up to 20 days, 6 weeks a week. Control mice received saline (vehicle) injections (n=10). Mice were sacrificed 20 days after cell injection and tumor size was measured. p=0.0043 for YHI1 (100 ng/kg) vs. control.

As shown in FIG. 13, YHI1 (100 ng/kg) significantly reduced local tumor growth by 55% (p=0.0043) while 30 ng/kg had a slightly weaker effect (17 days after cell injection). These results indicate that YHI1 is highly effective in inhibiting melanoma tumor growth.

Example 6

Effect of YHI1, YHI2 and YHI4 on Lung Metastasis in Mice Inoculated with 4T1 Mammary Carcinoma Cells YHI1 and its derivatives YHI2 and YHI4 were tested in comparison to a scrambled sequence (designated 'YHI3'), IIIM1 and Arg-Pbf. Table 2 summarizes the different compounds that were tested in this example. All peptides were synthesized to over 98% purity.

TABLE 2

Tested compounds

| Name | Sequence | Molecular weight | Dose* | SEQ ID NO: |
|---|---|---|---|---|
| YHI1 | KGHYAER(Pbf)VG | 1268 | 30 ng/kg | 1 |
| YHI2 | KGHYR(Pbf)AEVG | 1268 | 30 ng/kg | 2 |
| YHI3 | EAYHGKR(Pbf)GV | 1268 | 30 ng/kg | 3 |
| YHI4 | KGHYAER(NO$_2$)VG | 1062 | 24 ng/kg | 4 |
| IIIM1 | KGHYAERVG | 1016 | 24 ng/kg | 5 |
| Arg-Pbf | R(Pbf) | 425 | 10 ng/kg | - |

*The doses were calculated as molar equivalent to 30 ng/kg YHI1.

Female BALB/c mice (9-10 weeks old) were iv injected with 4T1 cells ($1 \times 10^4$ cells in 0.2 ml culture medium; medium was replaced with fresh medium one day prior to the injection). The tested compounds were ip administered on day 5 after tumor cell inoculation and continued daily thereafter 6 days a week until day 16, on which day the mice were sacrificed (in YHI3 group one animal died 14 days after cell injection before end of study). Each mouse received 10 injections during 11 consecutive days. A control group of mice received the same volume of saline (vehicle) injections. Each group contained 8 mice (n=8). Additional 4 mice remained naïve (without tumor cell injection and without any treatment), designated here as 'pure control'. At the end of the experiments the mice were sacrificed and their lungs were removed, weighed and quantified for number of foci.

Figure 14:
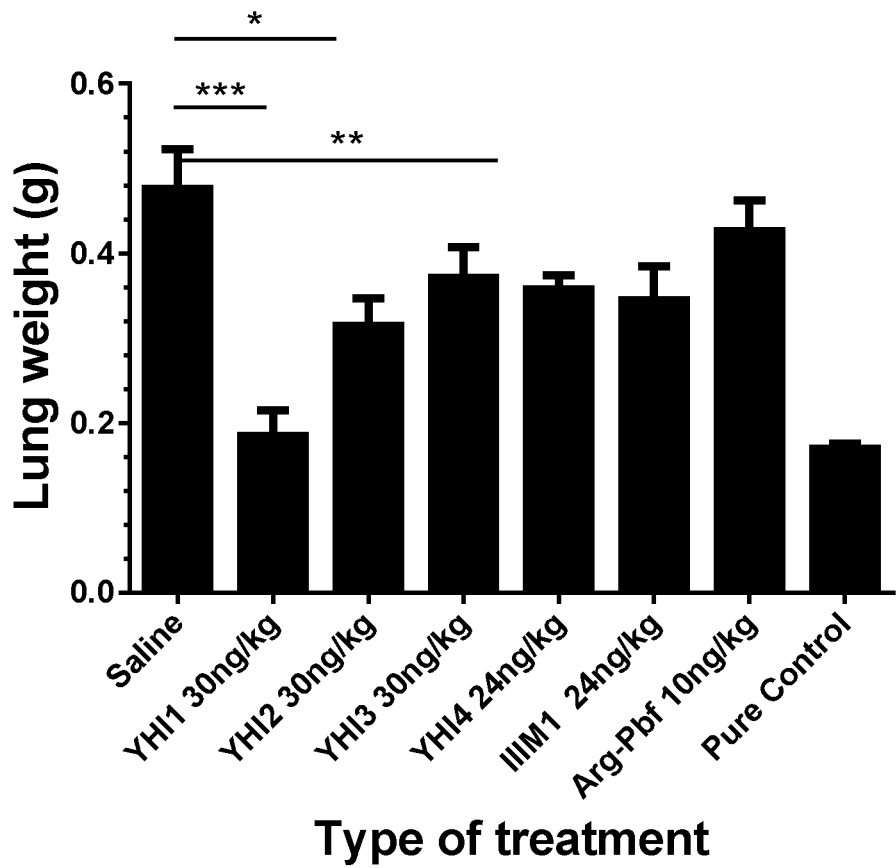
FIG. 14 shows the effect of YHI1, YHI2 and YHI4 on lung metastasis in mice inoculated with 4T1 mammary carcinoma cells, measured as a change in lung weight. Female BALB/c mice were i.v. injected with mammary 4T1 tumor cells. The tested peptides and control compounds YHI3, IIIM1 and Arg-Pbf were i.p. administered 5 days after cell injection at the indicated doses, and thereafter 6 days a week until day 16. Controls received the vehicle (saline). Additional 4 mice remained naïve ("pure control", no cell injection, no treatment). ***p=0.0001, *p=0.0127, **p=0.0307 for YHI1, YHI2 and YHI4 compared to saline, respectively.

As shown in FIG. 14, YHI1, YHI2 and YHI4 showed significant reduction in mice lung weight compared to control mice that received only saline (***p=0.0001, *p=0.0127, **p=0.0307 for YHI1, YHI2 and YHI4 compared to saline, respectively (student's t test) Results are expressed as mean±SE).

Figure 15:
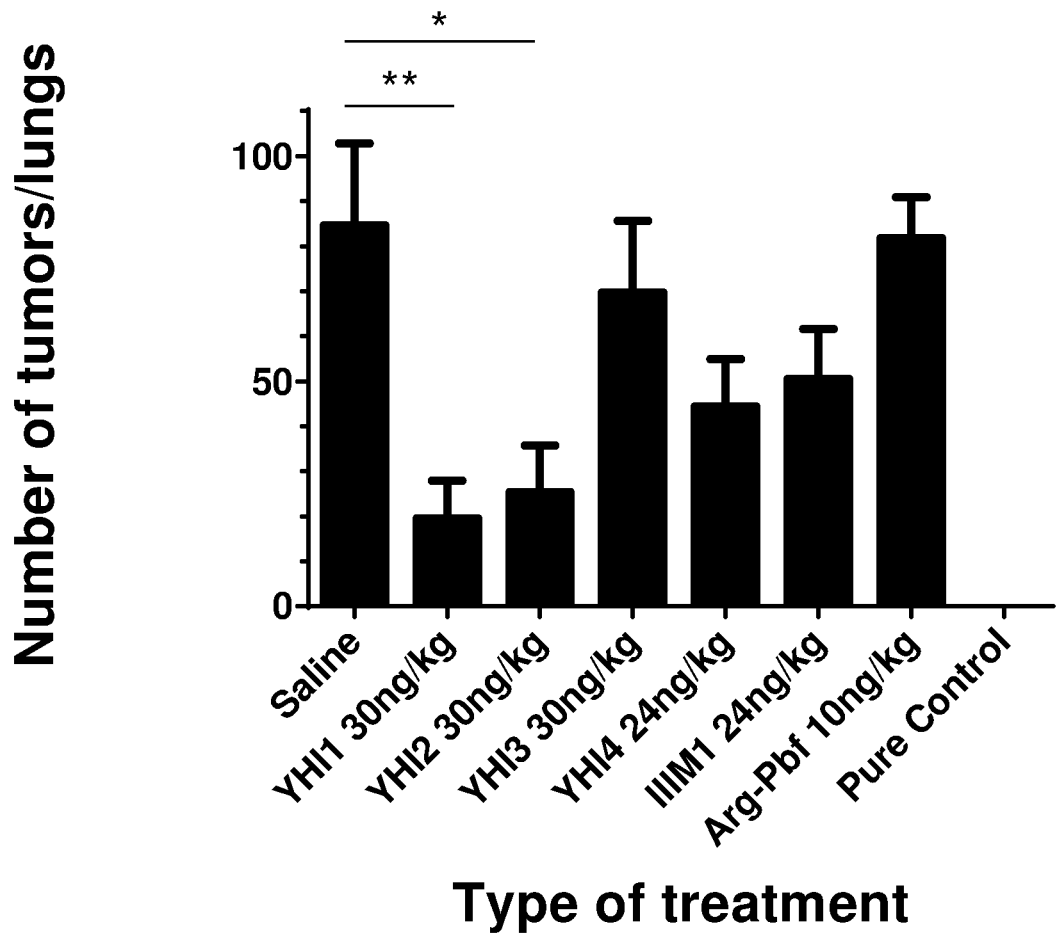
FIG. 15 shows the effect of YHI1, YHI2 and YHI4 on lung metastasis in mice inoculated with 4T1 mammary carcinoma cells, represented by the average number of lung foci. **p=0.0058, *p=0.0134 for YHI1 and YHI2 compared to saline, respectively.

As shown in FIG. 15, YHI1 and YHI2 showed significant reduction in the number of tumors per lung compared to control mice that received only saline (**p=0.0058, *p=0.0134 for YHI1 and YHI2 compared to saline, respectively (student's t test) Results are expressed as mean±SE). YHI4 also showed reduction in the number of tumors compared to control, but this reduction was not statistically significant.

The results demonstrate once again the efficiency of YHI1 in reducing mammary tumor cell (4T1) metastasis, and also demonstrate activity of two derivatives of YHI, namely, YHI2 and YHI4.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A peptide of 9-15 amino acids comprising the sequence Lys-Gly-His-Tyr-$X_1$-$X_2$-$X_3$-Val-Gly (SEQ ID NO: 6), wherein $X_1$-$X_2$-$X_3$ represents a sequence selected from the group consisting of Ala-Glu-Arg(Z), Ala-Arg(Z)-Glu and Arg(Z)-Ala-Glu, wherein Z is selected from the group consisting of Pbf (2,2,4,6,7-pentamethyldihydrobenzofuran-5-sulfonyl) and Nitro ($NO_2$), wherein the peptide is at least 95% pure.

2. The peptide of claim 1, comprising the sequence selected from the group consisting of:

```
                                              (SEQ ID NO: 1)
Lys-Gly-His-Tyr-Ala-Glu-Arg(Pbf)-Val-Gly;

(SEQ ID NO: 2)
Lys-Gly-His-Tyr-Arg(Pbf)-Ala-Glu-Val-Gly;
and (SEQ ID NO: 4)
Lys-Gly-His-Tyr-Ala-Glu-Arg(NO₂)-Val-Gly.
```

3. The peptide of claim 1, further comprising at least one modification selected from the group consisting of an amino-terminal modification and a carboxy-terminal modification.

4. The peptide of claim 1, wherein the peptide is of 9-12 amino acids.

5. The peptide of claim 1, wherein the peptide is of 9 amino acids.

6. The peptide of claim 1, selected from the group consisting of:

```
                                              (SEQ ID NO: 7)
R₁-Lys-Gly-His-Tyr-Ala-Glu-Arg(Pbf)-Val-Gly-R₂;

(SEQ ID NO: 8)
R₁-Lys-Gly-His-Tyr-Arg(Pbf)-Ala-Glu-Val-Gly-R₂;
and (SEQ ID NO: 9)
R₁-Lys-Gly-His-Tyr-Ala-Glu-Arg(NO₂)-Val-Gly-R₂,
``` wherein $R_1$ designates a hydrogen of an unmodified amino terminal group or is an amino blocking group selected from the group consisting of acyl and alkyl; and $R_2$ designates OH of an unmodified carboxy terminal group or is a carboxyl blocking group selected from the group consisting of an amide, alcohol and ester.

7. The peptide of claim 1, selected from the group consisting of:

```
                                              (SEQ ID NO: 1)
H-Lys-Gly-His-Tyr-Ala-Glu-Arg(Pbf)-Val-Gly-OH;

(SEQ ID NO: 2)
H-Lys-Gly-His-Tyr-Arg(Pbf)-Ala-Glu-Val-Gly-OH;
and (SEQ ID NO: 4)
H-Lys-Gly-His-Tyr-Ala-Glu-Arg(NO₂)-Val-Gly-OH.
```

8. A conjugate comprising the peptide of claim 1 and a moiety selected from the group consisting of a permeability enhancing moiety, a targeting moiety and a carrier moiety.

9. A pharmaceutical composition comprising the peptide of claim 1 and a pharmaceutically acceptable carrier, excipient or diluent.

10. A method for inhibiting cancer cell growth and metastasis in a subject in need thereof, the method comprising administering to the subject a pharmaceutical composition comprising a therapeutically effective amount of the peptide of claim 1.

11. The method of claim 10, wherein the cancer is a solid tumor.

12. The method of claim 11, wherein the solid tumor is selected from the group consisting of lung cancer, colon cancer, breast cancer, pancreatic cancer, prostate cancer, melanoma, and ovarian cancer.

13. The method of claim 10, wherein the cancer is a non-solid malignant disease.

14. A peptide selected from the group consisting of:

```
                                              (SEQ ID NO: 10)
R₁-Lys-Gly-His-Tyr-Ala-Glu-Arg(Z)-Val-Gly-R₂;

(SEQ ID NO: 11)
R₁-Lys-Gly-His-Tyr-Ala-Arg(Z)-Glu-Val-Gly-R₂;

(SEQ ID NO: 12)
R₁-Lys-Gly-His-Tyr-Arg(Z)-Ala-Glu-Val-Gly-R₂;

(SEQ ID NO: 13)
R₁-Lys-Gly-His-Arg(Z)-Tyr-Ala-Glu-Val-Gly-R₂;

(SEQ ID NO: 14)
R₁-Lys-Gly-Arg(Z)-His-Tyr-Ala-Glu-Val-Gly-R₂;

(SEQ ID NO: 15)
R₁-Lys-Arg(Z)-Gly-His-Tyr-Ala-Glu-Val-Gly-R₂;
and (SEQ ID NO: 16)
R₁-Lys-Gly-His-Tyr-Ala-Glu-Val-Arg(Z)-Gly-R₂;
``` wherein:
$R_1$ designates a hydrogen of an unmodified amino terminal group or is selected from the group consisting of: (i) an amino blocking group selected from acyl and alkyl, and (ii) a permeability-enhancing or targeting moiety;
$R_2$ designates OH of an unmodified carboxy terminal group or is selected from the group consisting of: (i) a carboxyl blocking group selected from the group consisting of an amide, alcohol and ester, and (ii) a permeability-enhancing or targeting moiety; and Z is selected from the group consisting of Pbf (2,2,4,6,7-pentamethyldihydrobenzofuran-5-sulfonyl) and Nitro ($NO_2$), wherein the peptide is at least 95% pure.

15. The peptide of claim 14, wherein the peptide is conjugated to a moiety selected from the group consisting of a fatty acid, a synthetic polymer, a carrier or targeting peptide, a carrier or targeting protein, and a sugar moiety.

16. A pharmaceutical composition comprising the peptide of claim 14 and a pharmaceutically acceptable carrier, excipient or diluent.

17. A method for inhibiting cancer cell growth and metastasis in a subject in need thereof, the method comprising administering to the subject a pharmaceutical composition comprising a therapeutically effective amount of the peptide of claim 14.

18. The method of claim 17, wherein the cancer is a solid tumor.

19. The method of claim 18, wherein the solid tumor is selected from the group consisting of lung cancer, colon cancer, breast cancer, pancreatic cancer, prostate cancer, melanoma, and ovarian cancer.

20. The method of claim 17, wherein the cancer is a non-solid malignant disease.

* * * * *